United States Patent [19]
Whittaker et al.

[11] Patent Number: 5,952,499
[45] Date of Patent: Sep. 14, 1999

[54] THERAPEUTIC COMPOUND-FATTY ACID CONJUGATES

[75] Inventors: Robert George Whittaker, West Pymble; Veronika Judith Bender, Cremorne; Wayne Gerrard Reilly, Northmead; Minoo Moghaddam, Killara, all of Australia

[73] Assignee: Commonwealth Scientific and Industrial Research Organisation, Campbell, Australia

[21] Appl. No.: 08/875,098

[22] PCT Filed: Jan. 15, 1996

[86] PCT No.: PCT/AU96/00015

§ 371 Date: Sep. 25, 1997

§ 102(e) Date: Sep. 25, 1997

[87] PCT Pub. No.: WO96/22303

PCT Pub. Date: Jul. 25, 1996

[30] Foreign Application Priority Data

| Jan. 16, 1995 | [AU] | Australia | PN 0580 |
|---|---|---|---|
| Jan. 16, 1995 | [AU] | Australia | PN 0581 |
| Jan. 16, 1995 | [AU] | Australia | PN 0582 |
| Jan. 16, 1995 | [AU] | Australia | PN 0583 |
| Jan. 16, 1995 | [AU] | Australia | PN 0584 |
| Jan. 16, 1995 | [AU] | Australia | PN 0585 |
| Jan. 16, 1995 | [AU] | Australia | PN 0586 |

[51] Int. Cl.$^6$ ..................... A61K 31/495; A61K 31/505; C07D 475/00
[52] U.S. Cl. ..................... 544/260; 514/249; 514/258
[58] Field of Search ............... 544/260; 514/249, 514/258

[56] References Cited

U.S. PATENT DOCUMENTS

| 3,686,238 | 8/1972 | Zaffaroni . |
| 5,869,606 | 2/1999 | Whittaker . |

FOREIGN PATENT DOCUMENTS

| 65048/94 | 10/1994 | Australia . |
| 0457570A1 | 11/1991 | European Pat. Off. . |
| 43 11 987 | 10/1994 | Germany . |
| WO 89/07938 | 9/1989 | WIPO . |
| WO 90/00555 | 1/1990 | WIPO . |
| WO 91/09837 | 7/1991 | WIPO . |
| WO 93/02706 | 2/1993 | WIPO . |
| WO 95/04030 | 2/1995 | WIPO . |

OTHER PUBLICATIONS

V.V. Belogorodskii et al., "Synthesis, Structure, and Antitumor Activity of Some p–Substituted N, N–di(2–chloroethyl)–Anilines", Pharmaceutical Chemistry Journal, vol. 15, No. 3, Mar. 1981, pp. 163–167.

V.V. Belogorodskii et al., "Quantitative relation of antitumor activity and toxicity with the structure of some para–substituted N,N–di(2–chlorethyl) anilines", Chemical Abstracts, vol. 95, No. 21, Nov. 1981, pp. 26.

Kinsky et al., "Circumvention of the methotrexate transport system by methotrexate–phosphatidylethanolamine derivatives: effect of fatty acid chain length". Biochim. Biophys. Acta, vol. 921(1), pp. 96–103, 1987.

Haggerty, G.C. et al., "The Pharmacological Activity of the Fatty Acid Conjugate Palmitoylcodeine in the Rat", Research Communications in Substances of Abuse, vol. 7, nos. 3 and 4, 1986, pp. 113–131.

Hostetler K.Y. et al., "Synthesis and Antiretroviral Activity of Phospholipid Analogs of Azidothymidine and Other Antiviral Nucleosides", The Journal of Biological Chemistry, vol. 265, No. 11, Apr. 15, 1990, pp. 6112–6117.

Steim J.M. et al., "Lipid Conjugates of Antiretroviral Agents. I. Azidothymidine–Monophosphate–Diglyceride: Anti–HIV Activity, Physical Properties, and Interaction with Plasma Proteins", Biochemical and Biophysical Research Communications, vol. 171, No. 1, Aug. 31, 1990, pp. 451–457.

Whittaker R.G. et al., "A New Procedure for Coupling Peptides with Fats", Innovation and perspectives in solid phase synthesis: collected papers, second international symposium 1991, Ed. R. Epton, issued 1992, pp. 495–498.

Anel A. et al., "Cytotoxicity of Chlorambucil and Chlorambucil–Fatty Acid Conjugates Against Human Lymphomas and Normal Human Peripheral Blood Lymphocytes", Biochemical Pharmacology, vol. 40, No. 6, 1990, pp. 1193–1200.

Kinsky S.C. et al., "Circumvention of the methotrexate transport system by methotrexate–phosphatidylethanolamine derivatives: effect of fatty acid chain length", Biochimica et Biophysica Acta 921, 1987, pp. 96–103.

Primary Examiner—Jose' G. Dees
Assistant Examiner—Barbara Badio
Attorney, Agent, or Firm—McDermott, Will & Emery

[57] ABSTRACT

A methotrexate conjugated to 1–3 acyl groups derived from fatty acids. In particular the invention relates to altering the pharmacokinetic profile and mode of delivery of methotrexate by conjugating it to 1.2 or 3 acyl derivatives of fatty acids.

16 Claims, No Drawings

THERAPEUTIC COMPOUND-FATTY ACID CONJUGATES

This application is a 371 of PCT/AU96/00015 filed Jan. 15, 1996.

The present invention relates to a range of therapeutic compounds conjugated to one to three acyl groups derived from fatty acids. The therapeutic compounds are selected from the following group:

1. the corticosterone family of drugs;
2. opioids and opioid antagonists;
3. antiviral nucleosides, such as AZT;
4. cyclosporins and related cyclopeptides;
5. folate antagonists including methotrexate, folic acid and folic acid analogues;
6. catecholamine precursors, such as DOPA and Dopamine, and catecholamines, such as adrenaline, noradrenaline and derivatives; and
7. alkylating agents containing a carboxylic acid group, such as chlorambucil and melphalan.

In particular the present invention relates to altering the pharmacokinetic profile and mode of delivery of these therapeutic compounds by conjugating them to one to three acyl derivatives of fatty acids.

1. THE CORTICOSTERONE FAMILY OF DRUGS

Among the most commonly used therapeutic agents are the corticosterone family of drugs based on the naturally occurring hormones produced by the adrenal cortex. There are two major groups of corticosterone hormones with overlapping activities:

glucocorticoids—normal biological action is the regulation of carbohydrate metabolism, possess anti-inflammatory activity at higher levels.

mineralocorticoids—concerned with water and mineral metabolism.

The corticosterones, both natural and synthetic, are based on the cholesterol molecule and generally have the common structural features of a) an hydroxyacetyl at position 17 (—CO—CH$_2$OH)
b) a ketone group at position 3 (=O)
c) a double bond between atoms 4 and 5

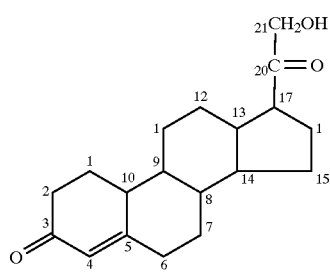

These groups are generally unmodified in active analogues of the hormones with the exception of the hydroxyl moiety (alternatively described as the hydroxyl at position 21) of the hydroxyacetyl at position 17 eg hydrocortisone acetate.

An example of a glucocorticoid is hydrocortisone (cortisol or 17 hydroxy corticosterone)

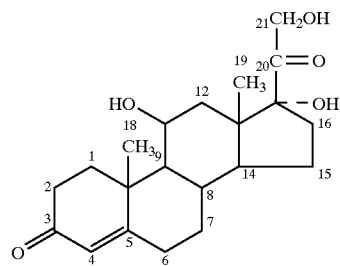

and of a mineralocorticoid is aldosterone.

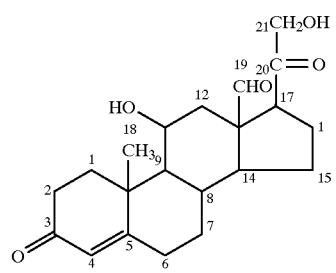

Of particular interest in one aspect of the present invention is the anti-inflammatory action of the glucocorticoids (both natural hormones and synthetic drugs) non-limiting examples of which are:

cortisone
hydrocortisone
fludrocortisone
prednisone
prednisolone
methylprednisolone
triamcinolone
dexamethasone
betamethasone
paramethasone
fluocinolone The present inventors have shown that members of this family can be linked to one to three acyl derivatives of fatty acids. It is believed that such new conjugated compounds are improved over the unconjugated therapeutic agent. Further it is believed that these novel compounds will aid in the oral, transdermal, intraarticular, intranasal, and/or intraocular delivery of these drugs.

Accordingly in a first aspect the present invention consists in a compound of the following formula:

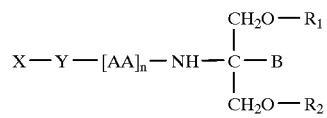

in which
X is a member of the corticosterone family of hormones or drugs and is linked to Y via an hydroxyl group
Y is a spacer group
AA is an amino acid; n is a number from 0 to 5
B is H or CH$_2$O—R$_3$
R$_1$, R$_2$ and R$_3$ are the same or different and are either hydrogen, methyl, ethyl or an acyl group derived from a fatty acid, with the proviso that at least one of $R_1$, $R_2$ and $R_3$ is an acyl group derived from a fatty acid.

In a second aspect the present invention consists in a compound of the following formula:

X—Y—[AA]$_n$—NH—CH$_2$—CH$_2$O—R$_4$ in which
X is a member of the corticosterone family of hormones or drugs and is linked to Y via an hydroxyl group
Y is a spacer group
AA is an amino acid; n is a number from 0 to 5, and
$R_4$ is an acyl group derived from a fatty acid.

In a third aspect the present invention consists in a method of prolonging or altering the activity of a member of the corticosterone family of hormones or drugs comprising administering the compound in the form:

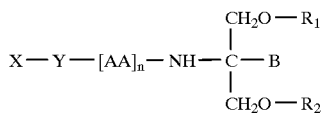

$$X-Y-[AA]_n-NH-\underset{\underset{CH_2O-R_2}{|}}{\overset{\overset{CH_2O-R_1}{|}}{C}}-B$$

in which
X is a member of the corticosterone family of hormones or drugs and is linked to Y via an hydroxyl group
Y is a linker group
AA is an amino acid; n is a number from 0 to 5
B is H or CH$_2$O—R$_3$
$R_1$, $R_2$ and $R_3$ are the same or different and are either hydrogen, methyl, ethyl or an acyl group derived from a fatty acid, with the proviso that at least one of $R_1$, $R_2$ and $R_3$ is an acyl group derived from a fatty acid.

In a fourth aspect the present invention consists in a method of prolonging or altering the activity of a member of the corticosterone family of hormones or drugs comprising administering the compounds in the form:

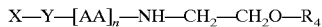

X—Y—[AA]$_n$—NH—CH$_2$—CH$_2$O—R$_4$ in which
X is a member of the corticosterone family of hormones or drugs and is linked to Y via an hydroxyl group
Y is a spacer group
AA is an amino acid; n is a number from 0 to 5, and
$R_4$ is an acyl group derived from a fatty acid.

The fatty acid may be saturated or unsaturated.

As stated above X is linked via a hydroxyl group to the linker Y. Typically, this hydroxyl group will be at position 17 or 21, however it may be at other positions such as 16.

Linkers Y to join compounds with an hydroxyl group to the amino group of Tris (when B is CH$_2$O—R$_3$) or the intervening amino acid (AA, if present) useful in the present invention include:

a) a linker with a carboxyl group to the compound and a carboxyl group to the Tris (or amino acid if present) such as a dicarboxylic acid via the anhydride eg succinic anhydride, maleic anhydride.

b) a linker with a carboxyl group to the compound and an aldehyde group to the Tris (or amino acid if present) such as glyoxylic acid (in the presence of a reducing agent eg NaBH$_4$).

c) a linker with a carboxyl group to the compound and an halide group to the Tris (or amino acid if present) such as chloroacetic acid.

d) a linker with a carboxyl group to the compound and a N=C=O group to the Tris (or amino acid if present) such as ethylisocyanatoacetate.

X may be any one of the members of the corticosterone family of compounds, however, it is presently preferred that X is hydrocortisone or cortisone.

In further preferred embodiments of this aspect of the present invention Y is a dicarboxylic acid, AA is not present or is glycine or alanine and the linkage is via the hydroxyl group at position 21.

As will be appreciated $R_1$, $R_2$ and $R_3$ are either hydrogen or an acyl group of a fatty acid. Also it is clear to those skilled in the art that substitutions other than methyl or ethyl are possible at $R_1$, $R_2$ and $R_3$. The prime requirement is that at least one of $R_1$, $R_2$ and $R_3$ is an acyl group derived from a fatty acid.

When $R_1$, $R_2$ and $R_3$ are each acyl groups of fatty acids it is preferred that they are the same group. It is also preferred that the acyl groups of fatty acids have a carbon chain of 3 to 18, more preferably 10 to 18.

It will be appreciated by those skilled in the art that similar modifications could be made to some members of the other classes of steroid (or analogues) hormones such as the male and female sex hormones at hydroxyl groups situated at various sites in the molecule.

The present invention also provides therapeutic compositions comprising the compound of the first or second aspect of the present invention and a pharmaceutically acceptable carrier. The composition may further include an unconjugated member of the corticosterone family of hormones or drugs.

The therapeutic composition may be administered by any appropriate route as will be recognised by those skilled in the art. Such routes include transdermal, intraarticular, oral, intranasal and intraocular.

2. OPIOIDS AND OPIOID ANTAGONISTS

Morphine is a classic example of an opiate analgesic that acts on the CNS receptors for the naturally occurring opioid peptides, the enkephalins and endorphins, mimicking their action. It is a powerful addictive drug used for the relief of moderate to severe pain associated with conditions such as heart attack, cancer, colic due to kidney or gall stones, following surgery and for severe burns etc. It has a short biological half-life and is normally delivered orally or by injection. Related opioid analgesic or antagonists include hydromorphone, oxymorphone, levorphanol, levallorphan, codeine, nalmefene, nalorphine, naloxone, naltrexone, buprenorphine, butorphanol and nalbufine.

Morphine has the structure:

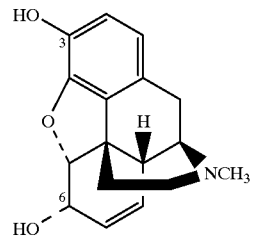

Modification of the hydroxyl groups at position 3 or 6 with lipophilic groups change the rate of absorption and distribution of morphine particularly to the CNS.

The present inventors have shown that morphine and related opioid analgesic or antagonists ("morphine family")

can be ester linked at the hydroxyl at the 3 position via spacers to one to three acyl derivatives of fatty acids. It is believed that such new conjugated compounds are improved over the unconjugated therapeutic agent. It is also believed that similar linkage could be achieved via the hydroxyl group at the 6 position.

Accordingly in a fifth aspect the present invention consists in a compound of the following formula:

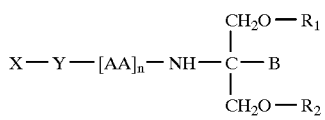

in which
X is a member of the morphine family and is linked to Y via an hydroxyl group eg the hydroxyl group at the 3 or 6 position
Y is a spacer group
AA is an amino acid; n is a number from 0 to 5
B is H or $CH_2O-R_3$
$R_1$, $R_2$ and $R_3$ are the same or different and are either hydrogen, methyl, ethyl or an acyl group derived from a fatty acid, with the proviso that at least one of $R_1$, $R_2$ and $R_3$ is an acyl group derived from a fatty acid.

In a sixth aspect the present invention consists in a compound of the following formula:

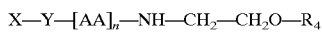

in which
X is a member of the morphine family and is linked to Y via an hydroxyl group at the 3 or 6 position
Y is a spacer group
AA is an amino acid; n is a number from 0 to 5, and
$R_4$ is an acyl group derived from a fatty acid.

In a seventh aspect the present invention consists in a method of prolonging or altering the activity of a member of the morphine family comprising administering the compound in the form:

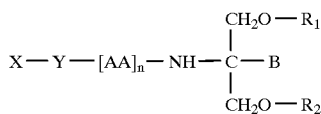

in which
X is a member of the morphine family and is linked to Y via an hydroxyl group at the 3 or the 6 position
Y is a linker group
AA is an amino acid; n is a number from 0 to 5
B is H or $CH_2O-R_3$
$R_1$, $R_2$ and $R_3$ are the same or different and are either hydrogen, methyl, ethyl or an acyl group derived from a fatty acid, with the proviso that at least one of $R_1$, $R_2$ and $R_3$ is an acyl group derived from a fatty acid.

In an eighth aspect the present invention consists in a method of prolonging or altering the activity of a member of the morphine family comprising administering the compound in the form:

in which
X is a member of the morphine family and is linked to Y via an hydroxyl group at the 3 or the 6 position
Y is a spacer group
AA is an amino acid; n is a number from 0 to 5, and
$R_4$ is an acyl group derived from a fatty acid.
The fatty acid may be saturated or unsaturated.
Linkers Y to join compounds with an hydroxyl group to the amino group of Tris (when B is $CH_2O-R_3$) or the intervening amino acid (AA, if present) useful in the present invention include:
a) a linker with a carboxyl group to the compound and a carboxyl group to the Tris (or amino acid if present) such as a dicarboxylic acid via the anhydride eg succinic anhydride, maleic anhydride.
b) a linker with a carboxyl group to the compound and an aldehyde group to the Tris (or amino acid if present) such as glyoxylic acid (in the presence of a reducing agent eg $NaBH_4$).
c) a linker with a carboxyl group to the compound and an halide group to the Tris (or amino acid if present) such as chloroacetic acid.
d) a linker with a carboxyl group to the compound and a N=C=O group to the Tris (or amino acid if present) such as ethylisocyanatoacetate.

In a preferred embodiment of the present invention X is morphine modified at the 3 or 6 position, Y is a dicarboxylic acid and AA is not present or is glycine or alanine.

As stated above $R_1$, $R_2$ and $R_3$ are either hydrogen or an acyl group of a fatty acid. Also it will be clear to those skilled in the art that substitutions other than methyl or ethyl are possible at $R_1$, $R_2$ and $R_3$. The prime requirement is that at least one of $R_1$, $R_2$ and $R_3$ is an acyl group derived from a fatty acid.

When $R_1$, $R_2$ and $R_3$ are acyl groups of fatty acids it is preferred that they are the same group. It is also preferred that the acyl groups of fatty acids have a carbon chain of 3 to 18, more preferably 10 to 18.

The present invention also provides therapeutic compositions comprising the compound of the fifth or sixth aspect of the present invention and a pharmaceutically acceptable carrier. The composition may further include an unconjugated member of the morphine family.

The therapeutic composition may be administered by any appropriate route as will be recognised by those skilled in the art. Such routes include topical, local injection, intraperitoneal and intravenous.

3. ANTIVIRAL NUCLEOSIDES

As stated above in one aspect the present invention relates to therapeutic conjugates of AZT (azidothymidine or zidovudine) and other antiviral nucleosides (eg acyclovir, ganciclovir, vidarabine, idoxuridine, triphuridine, valaciclovir, famciclovir) and comprises the antiviral agents bound via linker group/s to one to three acyl groups and to methods involving the use of these compounds. In particular the present invention relates to alteration of the pharmacokinetics and/or mode of delivery and targeting of these drugs when bound to one to three acyl derivatives of fatty acids.

AZT is an example of an antiretroviral drug. It is active against human immunodeficiency virus (HIV) and other mammalian retroviruses. The drug is a thymidine analogue which is converted to the triphosphate derivative by normal cellular enzymes. In this form it inhibits viral reverse transcription (RNA dependent DNA synthesis). DNA chains are terminated by the incorporation of the modified thymidine. AZT is widely prescribed for AIDS and, as it has a short biological half-life, it must be administered every 4 hours. Its use is associated with many side effects from nausea to suppression of new blood cell formation and associated conditions.

AZT has the structure:

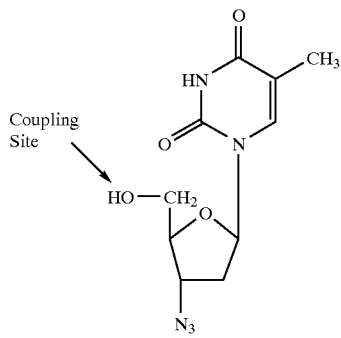

The present inventors have shown that AZT and similar drugs (hereafter termed "the Antiviral Nucleosides") can be linked to one to three acyl derivatives of fatty acids. It is believed that such new compounds will improve the delivery, uptake, half-life and targeting within the cell of the drug after oral, intranasal, transdermal, intraocular and other modes of delivery. Further it may change the distribution of the drug in the body increasing the percentage of drug delivered to the CNS and to lymphocytes in the lymphatic system.

Accordingly in a ninth aspect the present invention consists in a compound of the following formula:

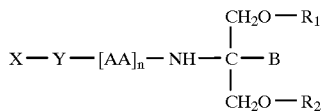

in which
X is an antiviral nucleoside and is linked to Y via an hydroxyl group
Y is a spacer group
AA is an amino acid; n is a number from 0 to 5
B is H or $CH_2O-R_3$
$R_1$, $R_2$ and $R_3$ are the same or different and are either hydrogen, methyl, ethyl or an acyl group derived from a fatty acid, with the proviso that at least one of $R_1$, $R_2$ and $R_3$ is an acyl group derived from a fatty acid.

In a tenth aspect the present invention consists in a compound of the following formula:

in which
X is an antiviral nucleoside and is linked to Y via an hydroxyl group
Y is a spacer group
AA is an amino acid; n is a number from 0 to 5, and
$R_4$ is an acyl group derived from a fatty acid.

In a eleventh aspect the present invention consists in a method of prolonging or altering the activity of an antiviral nucleoside comprising administering the antiviral nucleoside in the form:

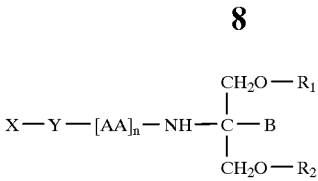

in which
X is an antiviral nucleoside and is linked to Y via an hydroxyl group
Y is a linker group
AA is an amino acid; n is a number from 0 to 5
B is H or $CH_2O-R_3$
$R_1$, $R_2$ and $R_3$ are the same or different and are either hydrogen, methyl, ethyl or an acyl group derived from a fatty acid, with the proviso that at least one of $R_1$, $R_2$ and $R_3$ is an acyl group derived from a fatty acid.

In a twelfth aspect the present invention consists in a method of prolonging or altering the activity of an antiviral nucleoside comprising administering the antiviral nucleoside in the form:

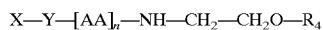

in which
X is an antiviral nucleoside and is linked to Y via an hydroxyl group
Y is a spacer group
AA is an amino acid; n is a number from 0 to 5, and
$R_4$ is an acyl group derived from a fatty acid.

The fatty acid may be saturated or unsaturated.

Linkers Y to join compounds with an hydroxyl group to the amino group of Tris (when B is $CH_2O-R_3$) or the intervening amino acid (AA, if present) useful in the present invention include:

a) a linker with a carboxyl group to the compound and a carboxyl group to the Tris (or amino acid if present) such as a dicarboxylic acid via the anhydride eg succinic anhydride, maleic anhydride.

b) a linker with a carboxyl group to the compound and an aldehyde group to the Tris (or amino acid if present) such as glyoxylic acid (in the presence of a reducing agent eg $NaBH_4$).

c) a linker with a carboxyl group to the compound and an halide group to the Tris (or amino acid if present) such as chloroacetic acid.

d) a linker with a carboxyl group to the compound and a N=C=O group to the Tris (or amino acid if present) such as ethylisocyanatoacetate.

In a preferred embodiment of the present invention X is AZT, acyclovir, ganciclovir, vidarabine, idoxuridine, trifluridine, ddI, ddC, ddA, or ribavirin, however, it is presently preferred that X is AZT. It is also preferred that Y is a dicarboxylic acid and AA is not present or is glycine or alanine.

As stated above $R_1$, $R_2$ and $R_3$ are either hydrogen or an acyl group of a fatty acid. Also it will be clear to those skilled in the art that substitutions other than methyl or ethyl are possible at $R_1$, $R_2$ and $R_3$. The prime requirement is that at least one of $R_1$, $R_2$ and $R_3$ is an acyl group derived from a fatty acid.

When $R_1$, $R_2$ and $R_3$ are acyl groups of fatty acids it is preferred that they are the same group. It is also preferred that the acyl groups of fatty acids have a carbon chain of 3 to 18, more preferably 10 to 18.

The present invention also provides therapeutic compositions comprising the compound of the ninth or tenth aspect of the present invention and a pharmaceutically acceptable carrier. The composition may further include an unconjugated antiviral nucleoside.

The therapeutic composition may be administered by any appropriate route as will be recognised by those skilled in the art. Such routes include oral, intranasal, transdermal and intraocular.

4. CYCLOSPORINS AND RELATED CYCLOPEPTIDES

Cyclosporins are a family of closely related cyclic peptides which exhibit powerful immunosuppressive activity. Cyclosporins are used extensively (often in combination with glucocorticoids such as prednisolone) in organ transplantation to prevent rejection. Cyclosporins appear to act in a reversible manner on helper T lymphocytes by inhibiting the production of interleukins and interferons and/or inhibiting interleukin binding with receptors on killer T lymphocytes, thereby curtailing the cell mediated response to the foreign cells of the transplanted tissue or organ. Animal studies have shown that cyclosporins inhibit a range of immune responses including delayed cutaneous hypersensitivity, Freund's adjuvant induced arthritis and T cell dependent antibody production opening the possibility of use in a broader range of applications than is currently practiced eg topically applied cyclosporin could be beneficial in the treatment of psoriasis and/or arthritis.

The structure of the cyclosporin family is shown below with cyclosporins A, B, C, D, and G varying only at side-chain R.

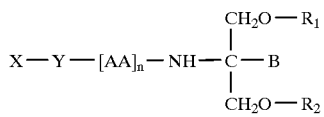

in which

X is a member of the cyclosporin family of drugs and is linked to Y via an hydroxyl group Y is a spacer group AA is an amino acid; n is a number from 0 to 5

B is H or $CH_2O$—$R_3$ $R_1$, $R_2$ and $R_3$ are the same or different and are either hydrogen, methyl, ethyl or an acyl group derived from a fatty acid, with the proviso that at least one of $R_1$, $R_2$ and $R_3$ is an acyl group derived from a fatty acid.

In a fourteenth aspect the present invention consists in a compound of the following formula:

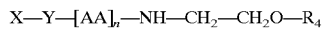

in which

X is a member of the cyclosporin family of drugs and is linked to Y via an hydroxyl group Y is a spacer group AA is an amino acid; n is a number from 0 to 5, and $R_4$ is an acyl group derived from a fatty acid.

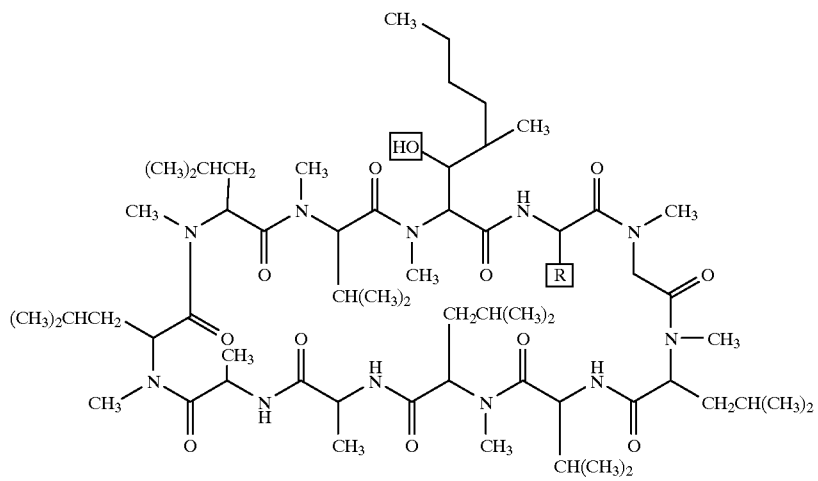

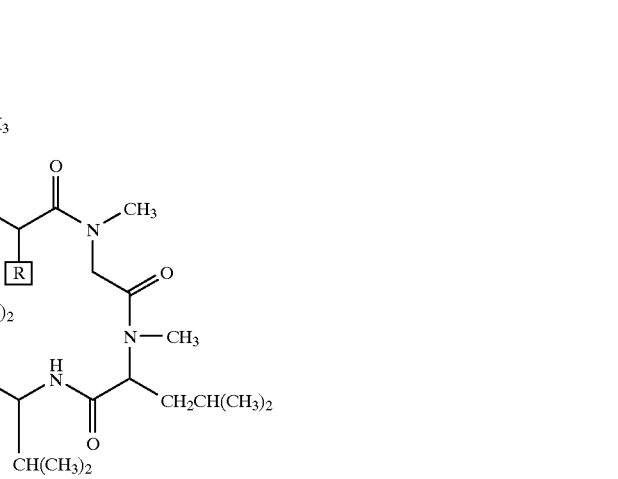

The present inventors propose that members of this family can be linked to one to three acyl derivatives of fatty acids. This could be possible by linkage to the invariant hydroxyl group or via linkage to variants of R eg cyclosporin C has a threonine side chain at R which could be used as a linkage point. It is believed that such new compounds will improve the delivery, uptake, half-life and/or mode of delivery of the members of the cyclosporin family of drugs. Further it is believed that these novel compounds will aid in the oral, transdermal, intranasal, parenteral and/or intraocular delivery of these drugs by facilitating their transport across lipophilic membranes.

Accordingly in a thirteenth aspect the present invention consists in a compound of the following formula:

In a fifteenth aspect the present invention consists in a method of prolonging or altering the activity of a member of the cyclosporin family of drugs comprising administering the compound in the form:

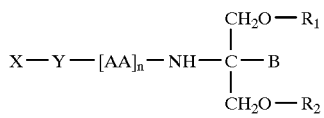

in which

X is a member of the cyclosporin family of drugs and is linked to Y via an hydroxyl group Y is a linker group AA is an amino acid; n is a number from 0 to 5

B is H or CH$_2$O—R$_3$

R$_1$, R$_2$ and R$_3$ are the same or different and are either hydrogen, methyl, ethyl or an acyl group derived from a fatty acid, with the proviso that at least one of R$_1$, R$_2$ and R$_3$ is an acyl group derived from a fatty acid.

In a sixteenth aspect the present invention consists in a method of prolonging or altering the activity of a member of the cyclosporin family of drugs comprising administering the compound in the form:

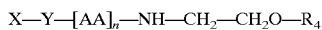

in which

X is a member of the cyclosporin family of drugs or related cyclopeptide and is linked to Y via an hydroxyl group Y is a spacer group AA is an amino acid; n is a number from 0 to 5, and R$_4$ is an acyl group derived from a fatty acid.

Where X is a member of the cyclosporin family of drugs it may be linked to Y via the invariant hydroxyl moiety of the family or the hydroxyl group of the threonine side-chain of cyclosporin C. Alternatively, as opposed to linking solely via an hydroxyl, specific new analogues could be produced with a range of reactive side chains at this position.

The fatty acid may be saturated or unsaturated.

Linkers Y to join compounds with an hydroxyl group to the amino group of Tris (when B is CH$_2$O—R$_3$) or the intervening amino acid (AA, if present) useful in the present invention include:

a) a linker with a carboxyl group to the compound and a carboxyl group to the Tris (or amino acid if present) such as a dicarboxylic acid via the anhydride eg succinic anhydride, maleic anhydride.

b) a linker with a carboxyl group to the compound and an aldehyde group to the Tris (or amino acid if present) such as glyoxylic acid (in the presence of a reducing agent eg NaBH$_4$).

c) a linker with a carboxyl group to the compound and an halide group to the Tris (or amino acid if present) such as chloroacetic acid.

d) a linker with a carboxyl group to the compound and a N=C=O group to the Tris (or amino acid if present) such as ethylisocyanatoacetate.

It is preferred that X is a member of the cyclosporin family, preferably cyclosporin C. It is also preferred that Y is a dicarboxylic acid and AA is not present or is glycine or alanine.

As stated above R$_1$, R$_2$ and R$_3$ are either hydrogen or an acyl group of a fatty acid. It is also be clear to those skilled in the art that substitutions other than methyl or ethyl are possible at R$_1$, R$_2$ and R$_3$. The prime requirement is that at least one of R$_1$, R$_2$ and R$_3$ is an acyl group derived from a fatty acid.

When R$_1$, R$_2$ and R$_3$ are acyl groups of fatty acids it is preferred that they are the same group. It is also preferred that the acyl groups of fatty acids have a carbon chain of 3 to 18, more preferably 10 to 18.

The present invention also provides therapeutic compositions comprising the compound of the thirteenth or fourteenth aspect of the present invention and a pharmaceutically acceptable carrier. The composition may further include an unconjugated member of the cyclosporin family of drugs or related cyclopeptides.

The therapeutic composition may be administered by any appropriate route as will be recognised by those skilled in the art. Such routes include oral, transdermal, intranasal, parenteral and intraocular.

5. FOLATE ANTAGONISTS INCLUDING METHOTREXATE, FOLIC ACID AND FOLIC ACID ANALOGUES

Methotrexate, an anti-metabolite drug, is an example of the folate antagonist family of drugs. It acts to reduce the proliferation of new cells by acting as a competitive inhibitor of folic acid reductase thereby preventing the conversion of the vitamin folic acid to its active form, folinic acid. Methotrexate is prescribed for the treatment of cancers and is also used to reduce the proliferation of epithelial cells for treatment of psoriasis that is unresponsive to other forms of treatment. Low dose methotrexate is found to be effective in arresting the progress and relieving the symptoms of rheumatoid arthritis presumably by inhibition of the inflammatory cell response.

The present inventors have shown that members of the methotrexate family can be linked to one to three acyl derivatives of fatty acids. It is believed that such new compounds will improve the delivery, uptake, persistence in the intraarticular regions, half-life and/or mode of delivery and distribution into the CNS of these drugs. Further it is believed that these novel compounds will aid in their oral, intranasal, transdermal, intratumoural, parenteral, intraarticular and/or intraocular delivery.

Methotrexate

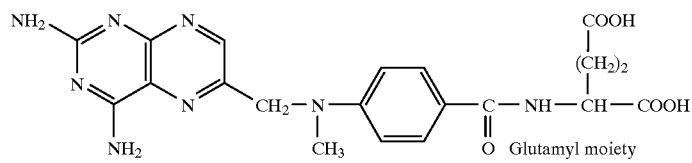

Accordingly in a seventeenth aspect the present invention consists in a compound of the following formula:

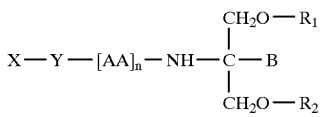

in which

X is a member of the folate antagonist family and is linked to Y via a carboxyl group Y is an optional spacer group AA is an amino acid; n is a number from 0 to 5

B is H or CH$_2$O—R$_3$

R$_1$, R$_2$ and R$_3$ are the same or different and are either hydrogen, methyl, ethyl or an acyl group derived from a fatty acid, with the proviso that at least one of $R_1$, $R_2$ and $R_3$ is an acyl group derived from a fatty acid.

In an eighteenth aspect the present invention consists in a compound of the following formula:

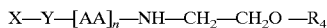
X—Y—[AA]$_n$—NH—CH$_2$—CH$_2$O —R$_4$ in which

X is a member of the folate antagonist family and is linked to Y via a carboxyl group Y is an optional spacer group AA is an amino acid; n is a number from 0 to 5, and R$_4$ is an acyl group derived from a fatty acid.

In a nineteenth aspect the present invention consists in a method of prolonging or altering the activity of a member of the folate antagonist family comprising administering the compound in the form:

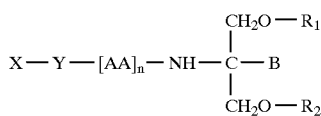

in which

X is a member of the folate antagonist family and is linked to Y via a carboxyl group Y is an optional spacer group AA is an amino acid; n is a number from 0 to 5

B is H or CH$_2$O—R$_3$ $R_1$, $R_2$ and $R_3$ are the same or different and are either hydrogen, methyl, ethyl or an acyl group derived from a fatty acid, with the proviso that at least one of $R_1$, $R_2$ and $R_3$ is an acyl group derived from a fatty acid.

In a twentieth aspect the present invention consists in a method of prolonging or altering the activity of a member of the folate antagonist family comprising administering the compound in the form:

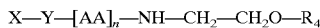
X—Y—[AA]$_n$—NH—CH$_2$—CH$_2$O—R$_4$ in which

X is a member of the folate antagonist family and is linked to Y via a carboxyl group Y is an optional spacer group AA is an amino acid; n is a number from 0 to 5, and R$_4$ is an acyl group derived from a fatty acid.

The fatty acid may be saturated or unsaturated.

Linkers Y to join compounds (such as methotrexate) with a carboxyl group to the amino group of Tris (when B is CH$_2$O—R$_3$) or the intervening amino acid (AA, if present) useful in the present invention include:

a) a linker with an amino group to the compound and a carboxyl group to the Tris (or amino acid if present) such as an amino acid or antibiotic.

b) a linker with an amino group to the compound and a sulphonic acid group to the Tris (or amino acid if present) such as 2-aminoethanesulphonic acid (taurine).

c) a linker with an hydroxyl group to the compound and a carboxyl group to the Tris (or amino acid if present) such as glycolic acid, lactic acid etc.

d) a linker with an hydroxyl group to the compound and a sulphonic acid group to the Tris (or amino acid if present) such as 2-hydroxyethanesulphonic acid (isethonic acid).

e) a linker with an hydroxyl group to the compound and a reactive halide group to the Tris (or amino acid if present) such as 2-chloroethanol.

f) other examples of potentially suitable linkers between a compound with a reactive carboxyl and the amino group of Tris (or amino acid if present) include the compound families exemplified by p-hydroxybenzaldehyde, 2-chloroacetic acid, 1,2-dibromoethane and ethyleneoxide.

In a preferred embodiment of the present invention X is methotrexate; Y is absent, an amino acid, glycolic acid, 3-hydroxypropionic acid or lactic acid, AA is not present or glycine or alanine, and the linkage is either an amide bond or an ester bond preferably to the γ-carboxyl of the glutamyl moiety of methotrexate.

As stated above $R_1$, $R_2$ and $R_3$ are either hydrogen, methyl, ethyl or an acyl group of a fatty acid. It will also be clear to those skilled in the art that substitutions other than methyl or ethyl are possible at $R_1$, $R_2$ and $R_3$. The prime requirement is that at least one of $R_1$, $R_2$ and $R_3$ is an acyl group derived from a fatty acid.

When $R_1$, $R_2$ and $R_3$ are acyl groups of fatty acids it is preferred that they are the same group. It is also preferred that the acyl groups of fatty acids have a carbon chain of 3 to 18, more preferably 10 to 18.

The present invention also provides therapeutic compositions comprising the compound of the seventeenth or eighteenth aspect of the present invention and a pharmaceutically acceptable carrier. The composition may further include an unconjugated member of the folate antagonist family.

The therapeutic composition may be administered by any appropriate route as will be recognised by those skilled in the art. Such routes include oral, intranasal, transdermal, intratumoural, parenteral, intraarticular and intraocular.

6. CATECHOLAMINE PRECURSORS AND CATECHOLAMINES

DOPA is a precursor of the catecholamines, an important pharmacologically active group of compounds including adrenaline, noradrenaline and dopamine; the neurotransmitter amines which act as adrenergic stimulants and vasopressor agents. DOPA and analogues (hereafter termed the DOPA family) diminishes akinesia in Parkinson's disease, probably acting to elevate dopamine levels in the brain.

A The present inventors have shown that DOPA can be linked to one to three acyl derivatives of fatty acids. It is believed that such new compounds will improve the delivery of DOPA across the gastrointestinal tract and the blood-brain barrier and improve its half-life. Further it is believed that these novel compounds will aid in the oral, transdermal, intranasal, parenteral and/or intraocular delivery of this drug.

Dopa

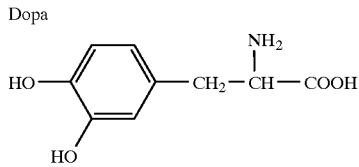

Accordingly in a twenty-first aspect the present invention consists in a compound of the following formula:

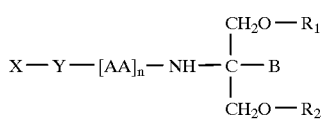

in which
- X is a member of the DOPA family and is linked to Y via a carboxyl group or an amino group
- Y is an optional spacer group
- AA is an amino acid; n is a number from 0 to 5
- B is H or $CH_2O-R_3$
- $R_1$, $R_2$ and $R_3$ are the same or different and are either hydrogen, methyl, ethyl or an acyl group derived from a fatty acid, with the proviso that at least one of $R_1$, $R_2$ and $R_3$ is an acyl group derived from a fatty acid.

In a twenty-second aspect the present invention consists in a compound of the following formula:

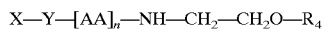

in which
- X is a member of the DOPA family and is linked to Y via a carboxyl group or an amino group
- Y is an optional spacer group
- AA is an amino acid; n is a number from 0 to 5, and
- $R_4$ is an acyl group derived from a fatty acid.

In a twenty-third aspect the present invention consists in a method of prolonging or altering the activity of a member of the DOPA family comprising administering it in the form:

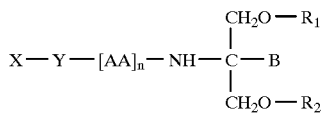

in which
- X is a member of the DOPA family and is linked to Y via a carboxyl group or an amino group
- Y is an optional spacer group
- AA is an amino acid; n is a number from 0 to 5
- B is H or $CH_2O-R_3$
- $R_1$, $R_2$ and $R_3$ are the same or different and are either hydrogen, methyl, ethyl or an acyl group derived from a fatty acid, with the proviso that at least one of $R_1$, $R_2$ and $R_3$ is an acyl group derived from a fatty acid.

In a twenty-fourth aspect the present invention consists in a method of prolonging or altering the activity of a member of the DOPA family comprising administering it in the form:

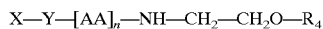

in which
- X is a member of the DOPA family and is linked to Y via a carboxyl group or an amino group
- Y is an optional spacer group
- AA is an amino acid; n is a number from 0 to 5, and
- $R_4$ is an acyl group derived from a fatty acid.

The fatty acid may be saturated or unsaturated.

Linkers Y to join compounds (such as DOPA) with a carboxyl group to the amino group of Tris (when B is $CH_2O-R_3$) or the intervening amino acid (AA, if present) useful in the present invention include:

a) a linker with an amino group to the compound and a carboxyl group to the Tris (or amino acid if present) such as an amino acid or antibiotic.

b) a linker with an amino group to the compound and a sulphonic acid group to the Tris (or amino acid if present) such as 2-aminoethanesulphonic acid (taurine).

c) a linker with an hydroxyl group to the compound and a carboxyl group to the Tris (or amino acid if present) such as glycolic acid, lactic acid etc.

d) a linker with an hydroxyl group to the compound and a sulphonic acid group to the Tris (or amino acid if present) such as 2-hydroxyethanesulphonic acid (isethonic acid).

e) a linker with an hydroxyl group to the compound and a reactive halide group to the Tris (or amino acid if present) such as 2-chloroethanol.

f) other examples of potentially suitable linkers between a compound with a reactive carboxyl and the amino group of Tris (or amino acid if present) include the compound families exemplified by p-hydroxybenzaldehyde, 2-chloroacetic acid, 1,2-dibromoethane and ethyleneoxide.

Non limiting examples of linkers Y to join compounds (such as DOPA) with an amino group to the amino group of Tris (when $B=CH_2OR_3$) or the intervening amino acid (if present) useful in the present invention include bifunctional compounds such as:

a) a linker with a carboxyl group to the compound and a carboxyl group to the Tris (or the amino acid if present) such as a dicarboxylic acid via the anhydride e.g. succinic anhydride, maleic anhydride, etc. Similarly compounds with two sulphonic acid groups or two reactive halide groups may be used.

b) a linker with a carboxyl group to the compound and a sulphonic acid group to the Tris (or the amino acid if present) such as hydroxyethanesulphonic acid (isethonic acid), or with the sulphonic acid group to the compound and a carboxyl group to the Tris or the intervening amino acid (if present).

c) a linker with a carboxyl group to the compound and a reactive halide group to the Tris (or the amino acid if present) such as 2-chloro ethanol or with the reactive halide to the compound and a carboxyl group to the Tris or the intervening amino acid (if present).

d) a linker with a reactive halide group to the compound and a sulphonic acid group to the Tris, or the amino acid (if present) or with the sulphonic acid group to the compound and the reactive halide to Tris or the intervening amino acid (if present).

In a preferred embodiment of the present invention X is DOPA. Y is absent, an amino acid, glycolic acid, 3-hydroxypropionic acid or lactic acid, AA is not present or glycine or alanine, and the linkage is either an amide bond or an ester bond to the carboxyl group.

As stated above $R_1$, $R_2$ and $R_3$ are either hydrogen or an acyl group of a fatty acid. It is also be clear to those skilled in the art that substitutions other than methyl or ethyl are possible at $R_1$, $R_2$ and $R_3$. The prime requirement is that at least one of $R_1$, $R_2$ and $R_3$ is an acyl group derived from a fatty acid.

When $R_1$, $R_2$ and $R_3$ are acyl groups of fatty acids it is preferred that they are the same group. It is also preferred that the acyl groups of fatty acids have a carbon chain of 3 to 18, more preferably 10 to 18.

The present invention also provides therapeutic compositions comprising the compound of the twenty-first or twenty-second aspect of the present invention and a pharmaceutically acceptable carrier. The composition may further include an unconjugated member of the DOPA family.

The therapeutic composition may be administered by any appropriate route as will be recognised by those skilled in the art. Such routes include oral, transdermal, intranasal, parenteral and intraocular.

7. ALKYLATING AGENTS CONTAINING A CARBOXYLIC ACID GROUP

Chlorambucil is an example of this family of compounds. It is a bifunctional alkylating agent and acts as a cytotoxic drug by cross-linking strands of DNA thereby preventing cell replication. Currently it is indicated for the treatment of Hodgkin's disease, certain forms of non-Hodgkin's lymphoma, certain leukaemias, ovarian and some breast cancers.

The present inventors have shown that chlorambucil and similar drugs can be linked to one to three acyl derivatives of fatty acids. It is believed that such new compounds will improve the delivery, uptake, half-life and/or mode of delivery of the drugs. Further it is believed that these novel compounds will aid in their oral, intranasal, transdermal, parenteral, intratumoural and/or intraocular delivery.

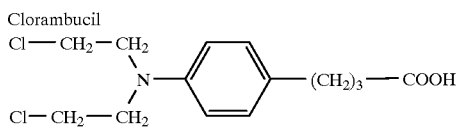

Accordingly in a twenty-fifth aspect the present invention consists in a compound of the following formula:

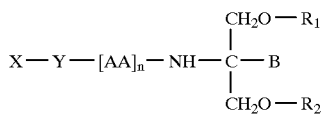

in which
X is a member of the chlorambucil family and is linked to Y via the carboxyl group
Y is an optional spacer group
AA is an amino acid; n is a number from 0 to 5
B is H or $CH_2O$—$R_3$
$R_1$, $R_2$ and $R_3$ are the same or different and are either hydrogen, methyl, ethyl or an acyl group derived from a fatty acid, with the proviso that at least one of $R_1$, $R_2$ and $R_3$ is an acyl group derived from a fatty acid.

In a twenty-sixth aspect the present invention consists in a compound of the following formula:

in which
X is a member of the chlorambucil family and is linked to Y via the carboxyl group
Y is an optional spacer group
AA is an amino acid; n is a number from 0 to 5, and
$R_4$ is an acyl group derived from a fatty acid.

In a twenty-seventh aspect the present invention consists in a method of prolonging or altering the activity of a compound which is a member of the chlorambucil family comprising administering the compound in the form:

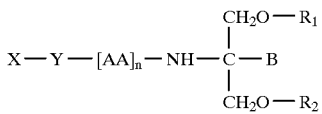

in which
X is a member of the chlorambucil family and is linked to Y via the carboxyl group
Y is an optional spacer group
AA is an amino acid; n is a number from 0 to 5
B is H or $CH_2O$—$R_3$
$R_1$, $R_2$ and $R_3$ are the same or different and are either hydrogen, methyl, ethyl or an acyl group derived from a fatty acid, with the proviso that at least one of $R_1$, $R_2$ and $R_3$ is an acyl group derived from a fatty acid.

In a twenty-eighth aspect the present invention consists in a method of prolonging or altering the activity of a compound which is a member of the chlorambucil family comprising administering the compound in the form:

in which
X is a member of the chlorambucil family and is linked to Y via the carboxyl group
Y is an optional spacer group
AA is an amino acid; n is a number from 0 to 5, and
$R_4$ is an acyl group derived from a fatty acid.

The fatty acids may be saturated or unsaturated.

Linkers Y to join compounds (such as chlorambucil) with a carboxyl group to the amino group of Tris (when B is $CH_2O$—$R_3$) or the intervening amino acid (AA, if present) useful in the present invention include:

a) a linker with an amino group to the compound and a carboxyl group to the Tris (or amino acid if present) such as an amino acid or antibiotic.

b) a linker with an amino group to the compound and a sulphonic acid group to the Tris (or amino acid if present) such as 2-aminoethanesulphonic acid (taurine).

c) a linker with an hydroxyl group to the compound and a carboxyl group to the Tris (or amino acid if present) such as glycolic acid, lactic acid etc.

d) a linker with an hydroxyl group to the compound and a sulphonic acid group to the Tris (or amino acid if present) such as 2-hydroxyethanesulphonic acid (isethonic acid).

e) a linker with an hydroxyl group to the compound and a reactive halide group to the Tris (or amino acid if present) such as 2-chloroethanol.

f) other examples of potentially suitable linkers between a compound with a reactive carboxyl and the amino group of Tris (or amino acid if present) include the compound families exemplified by p-hydroxybenzaldehyde, 2-chloroacetic acid, 1,2-dibromoethane and ethyleneoxide.

In a preferred embodiment of the present invention X is chlorambucil, Y is absent, an amino acid, glycolic acid, 3-hydroxypropionic acid or lactic acid, AA is not present or glycine or alanine and the linkage is either an amide bond or an ester bond to the carboxyl group.

As stated above $R_1$, $R_2$ and $R_3$ are either hydrogen or an acyl group of a fatty acid. It is also be clear to those skilled in the art that substitutions other than methyl or ethyl are possible at $R_1$, $R_2$ and $R_3$. The prime requirement is that at least one of $R_1$, $R_2$ and $R_3$ is an acyl group derived from a fatty acid.

When $R_1$, $R_2$ and $R_3$ are acyl groups of fatty acids it is preferred that they are the same group. It is also preferred that the acyl groups of fatty acids have a carbon chain of 3 to 18, more preferably 10 to 18.

The present invention also provides therapeutic compositions comprising the compound of the twenty-fifth or twenty-sixth aspect of the present invention and a pharmaceutically acceptable carrier. The composition may further include an unconjugated member of the chlorambucil family.

The therapeutic composition may be administered by any appropriate route as will be recognised by those skilled in the art. Such routes include oral, intranasal, transdermal, parenteral, intratumoural and intraocular.

In order that the nature of the present invention may be more clearly understood preferred forms thereof will now be described with reference to the following examples.

| Abbreviations used | |
|---|---|
| AZT | 3'-Azido-3'-deoxythymidine |
| DCC | 1,3-Dicyclohexylcarbodiimide |
| DCM | Dichloromethane |
| DCU | N,N'-Dicyclohexylurea |
| DIEA | N,N'-Diisopropylethylamine |
| DMAP | 4-Dimethylaminopyridine |
| DMF | Dimethylformamide |
| DOPA | 3-(3,4-dihydroxyphenyl)-alanine |
| DSC | N,N'-Disuccinimidyl carbonate |
| EtOAc | Ethyl acetate |
| Gly | Glycine |
| $GTP_1$ | Glycine-Tris-Monopalmitate |
| $GTP_2$ | Glycine-Tris-Dipalmitate |
| $GTP_3$ | Glycine-Tris-Tripalmitate |
| HOSu | N-Hydroxysuccinimide |
| HPLC | High performance liquid chromatography |
| 17-b Hydrocortisone | 17-Butyrate-Hydrocortisone |
| MeOH | Methanol |
| Mor | Morphine |
| MTX | Methotrexate |
| NMR | Nuclear Magnetic Resonance |
| Suc | Succinic Acid |
| TBDMS | tert.-Butyldimethylsilyl |
| TFA | Trifluoroacetic acid |
| THF | Tetrahydrofuran |
| TLC | Thin layer chromatography |
| TPTU | O-(1,2-Dihydro-2-oxo-1-pyridyl)-N,N,N',N'-tetramethyl-uronium tetrafluoroborate |
| Tris | 2-Amino-2-hydroxy-methyl-1,3 propanediol |
| TSTU | O—(N-Succinimidyl)-N,N,N',N'-tetramethyl-uronium tetrafluoroborate |
| Z | Benzyloxycarbonyl |

Analytical HPLC

Performed on Waters HPLC equipment using C18 Reverse Phase Columns (Radial Pak).

System I—For compounds without fatty acid moieties.

Buffer A—0.1% TFA in water.

Buffer B—80% acetonitrile: 20% water containing 0.1% TFA.

Gradient program from 30% B to 100% B over 5' maintained to 8'; flow 2 ml/min.

Retention Times—$R_tI$

System II—For hydrophobic compounds typically containing fatty acid moieties.

Buffer A—50% acetonitrile: 50% water containing 0.1% TFA.

Buffer B—50% acetonitrile: 50% THF containing 0.1% TFA.

Gradient program from 20% B to 100% B over 5' maintained to 8'; flow 2 ml/min.

Retention Times—$R_tII$

Preparation of Gly-Tris

The title compound was prepared by hydrogenation of a solution of Z-Gly-Tris in ethanol at 40 pa. pressure in a Parr hydrogenator in the presence of palladium on carbon (10%). The removal of the Z group was monitored by HPLC. The catalyst was removed by filtration and washed with ethanol. Evaporation of the solvent gave the title compound in 95% yield. The preparation of Z-Gly-Tris is described in Whittaker, R. G., Hayes, P. J., and Bender, V. J. (1993). Peptide Research 6; 125 and Australian Patent No. 649242.

EXAMPLE 1

Synthesis of Hydrocortisone-Suc-Gly-Tris-(Palmitate)$_n$: where n=1, 2 or 3.

I. Hydrocortisone-Succinate

To a solution of Hydrocortisone (3.65 g, 10 mmol) in acetonitrile (450 ml), succinic anhydride (1.65 g, 15 mmol) and DIEA (1.7 ml, 10 mmol) were added and the reaction mixture stirred at room temperature for 36 h. HPLC analysis of the reaction mixture showed 93% of the title compound. The solvent was evaporated and the residue redissolved in ethyl acetate and washed with water. The ethyl acetate phase was evaporated under reduced pressure and the residue triturated in diethyl ether to obtain 4.4 g of white powder in 95% yield. $R_tI$ 5.94'.

II. Hydrocortisone-Suc-OSu

To a solution of Hydrocortisone-succinate (4.0 g, 8.65 mmol) in acetonitrile (120 ml), DSC (4.43 g, 17.3 mmol) in 30 ml of DMF and DIEA (1 ml) were added. After 30 min a white precipitate was formed and HPLC analysis showed the formation of a new peak at 6.7' at 90%. The precipitate was filtered off to obtain 4 g of the title compound (100% pure by HPLC). The filtrate was evaporated and the residue triturated in acetonitrile and diethyl ether to obtain a further 0.6 g of the title compound. Total yield: 95%. $R_tI$ 6.7'.

III. Hydrocortisone-Suc-Gly-Tris

To a solution of Hydrocortisone-Suc-OSu (3.9 g, 7 mmol) in 20 ml of DMF, Gly-Tris (1.78 g, 10 mmol) in 20 ml of DMF was added and the reaction mixture stirred at room temperature. The title compound ($R_tI$ 4.98') was formed in 69% yield by HPLC analysis after 4 h. The solvent was removed under reduced pressure and the residue redissolved in 50 ml of ethyl acetate and washed with 100 ml of water. The water phase was evaporated to 20 ml and the title compound extracted with 200 ml of ethyl acetate (3 times) to obtain 2.4 g of the title compound at 95% purity by HPLC analysis; yield 56%, $R_tI$ 4.98'.

IV. Hydrocortisone-Suc-Gly-Tris-(Palmitate)$_n$; where n=1, 2 or 3

To a solution of Hydrocortisone-Suc-Gly-Tris (2.4 g, 3.85 mmol) in 100 ml of DCM and 10 ml of DMF, palmitic acid (2.46 g, 9.63 mmol) and a catalytic amount of DMAP were added and the reaction mixture cooled to 0° C. DCC (2.06 g, 10.02 mmol) in 20 ml of DCM was added to the reaction mixture by a dropping funnel. The reaction mixture was stirred at 0° C. for 30 min and then at room temperature. After 4 h of reaction a mixture of the title compound with 1, 2 or 3 palmitic acids (36%, 29%, 3.2% respectively) was formed. The solvents were evaporated and the residue redissolved in DCM. The DCU was filtered off and the filtrate evaporated to dryness. The residue was redissolved in a 1:1 mixture of acetonitrile and THF and separated by preparative HPLC using a C18 column (40×100 mm) to obtain 800 mg of Hydrocortisone-Suc-Gly-Tris-Mono palmitate, 1700 mg of Hydrocortisone-Suc-Gly-Tris-Dipalmitate and 230 mg of Hydrocortisone-Suc-Gly-Tris-Tripalmitate. Each conjugate was further purified on a silica column using a gradient from ethyl acetate:petroleum ether (60:40) to ethyl acetate:methanol (90:10).

EXAMPLE 2

Synthesis of 17-butyrate (17-b) Hydrocortisone-21-Suc-Gly-Tris-(Palmitate)$_n$; where n=1, 2 or 3.

I. 17-butyrate (17-b) Hydrocortisone-21-Succinate

To a solution of 17-b Hydrocortisone (2.16 g, 5 mmol) in acetonitrile (80 ml), succinic anhydride (1.25 g, 12.5 mmol) and DIEA (0.34 ml, 5 mmol) were added and the reaction mixture stirred at room temperature for 40 h. HPLC analysis of the reaction mixture showed up to 98% of the title compound. The solvent was evaporated and the residue redissolved in ethyl acetate and washed with water. The ethyl acetate phase was evaporated under reduced pressure and the residue triturated in diethyl ether to obtain 2.6 g of white powder in 95% yield.

II. 17-b Hydrocortisone-21-Suc-OSu

To a solution of 17-b Hydrocortisone-21-succinate (1.5 g, 2.8 mmol) in acetonitrile (40 ml), DSC (2.16 g, 7 mmol) in 30 ml of DMF and DIEA (0.47 ml) were added. After 1 h reaction at room temperature approximately 85% of the title compound was formed by HPLC analysis (100% pure by HPLC). The solvents were evaporated and the next step carried out without further purification.

III. 17-b Hydrocortisone-21-Suc-Gly-Tris

To a 20 ml DMF solution of 17-b Hydrocortisone-21-Suc-OSu (2.8 mmol), Gly-Tris (1.5 g, 8.4 mmol) in 20 ml of DMF was added and the reaction mixture stirred at room temperature. The title compound ($R_fI$ 6.09') was formed in 80% yield by HPLC analysis after 5 h. The solvent was removed under reduced pressure and the residue redissolved in 20 ml water/acetonitrile 50:50 and purified by preparative HPLC (Waters Prep4000 using a C18 column) to give 0.75 g of the title compound.

VI. 17-b Hydrocortisone-21-Suc-Gly-Tris-(Palmitate)$_n$; where n=1, 2 or 3

Palmitic acid (0.57 g, 2.22 mmol) and a catalytic amount of DMAP were added to a solution of 17-b Hydrocortisone-21-Suc-Gly-Tris (0.51 g, 0.74 mmol) in 20 ml of DCM and the reaction mixture cooled to 0° C. DCC (0.45 g, 2.22 mmol) in 10 ml of DCM was added to the reaction mixture dropwise. The reaction was stirred at 0° C. for 30 min and then at room temperature. After 2 h a mixture of the title compounds with 1, 2 or 3 palmitate groups (7%, 47%, 46% respectively by HPLC) was formed. The DCU was filtered off and the filtrate evaporated to dryness. The residue was redissolved in a 1:1 mixture of acetonitrile and THF. HPLC indicated that the solution contained a mixture of the title compounds in the ratio of 7:16:69; mono-; di-; tripalmitate. The mixture was separated by preparative HPLC using a C18 column (40×100 mm) to give 850 mg of 17-b Hydrocortisone-21-Suc-Gly-Tris-Tripalmitate, 150 mg of 17-b Hydrocortisone-21-Suc-Gly-Tris-Dipalmitate and 120 mg of the Monopalmitate. The Tripalmitate conjugate was 100% pure after preparative HPLC while the Mono and Dipalmitate conjugates needed further purification by silica chromatography using a gradient from ethyl acetate:petroleum ether (60:40) to ethyl acetate:methanol (90:10).

HPLC analysis indicated the title products to be of high purity, free from parent drug and other derivatives.

EXAMPLE 3

Synthesis of Morphine-Suc-Gly-Tris-Di and Tripalmitate.

The present inventors have demonstrated that the phenolic hydroxy group at the C-3 position of morphine (Mor) can be successfully coupled with Gly-Tris-Dipalmitate or Gly-Tris-Tripalmitate via a succinic acid (Suc) linker, without protection of the secondary hydroxy group at the C-6 position. The synthesis of Mor-Suc-Gly-Tris-Dipalmitate involved two steps with a 54% overall yield.

I. Preparation of Morphine-Succinate

Triethylamine (9.584 ml, 69.45 mmol) was added dropwise to a suspension of morphine sulphate (9.286 g, 27.78 mmol) in dry DMF (140 ml) at 0° C. under nitrogen. After stirring for ten minutes, succinic anhydride (2.781 g, 27.78 mmol) was added portionwise to the reaction. The reaction was monitored by TLC (50% EtOH/$H_2O$) and by analytical HPLC ($R_fI$ of Mor-Suc was 5.06'). The reaction was complete in 24 to 48 h and the product precipitated out. The precipitate was filtered and washed with a small volume of cold DMF and THF. Both $^1$H NMR and HPLC indicated that the product was of sufficient purity for the next reaction (Mor-Suc 6.11 g; 57% yield).

Preliminary $^1$H NMR indicated that succinylation occurred at the phenolic hydroxyl at the C-3 position.

II. Preparation of Morphine-Suc-Gly-Tris-Dipalmitate

General procedure of preparation of Mor-Suc-Gly-Tris-(Palmitate)$_n$.

To the suspension of Mor-Suc (0.860 g, 2.23 mmol) in dry THF (44 ml) at 0° C. under nitrogen, was added DCC (0.506 g, 2.45 mmol) and N-hydroxysuccinimide (0.308 g, 2.68 mmol). The resulting mixture was slowly warmed to room temperature, then refluxed overnight. The reaction was monitored by HPLC (System I); retention time of the active ester, Mor-Suc-OSu, was 5.45 min. After the reaction was completed, the mixture was cooled to 0° C. and the precipitate filtered off and washed with dry DCM. The filtrate was added directly to Gly-Tris-Dipalmitate (1.459 g, 2.23 mmol) at room temperature with vigorous stirring. The aminolysis of Mor-Suc-OSu was monitored by HPLC (System II) and TLC (10% MeOH/DCM). Both HPLC and TLC showed that the reaction was complete after stirring overnight. The solvent was removed under vacuum and the residue redissolved in DCM and washed with water several times until the pH equalled 7. The organic phase was dried ($MgSO_4$) and evaporated to afford a light yellow solid. The crude product was purified by the flash chromatography (silica, 10% MeOH/DCM) which gave the title compound (2.16 g) in excellent yield, (94.7%).

III. Preparation of Morphine-Suc-Gly-Tris Tripalmitate

Following the general procedure set out above Mor-Suc (0.101 g, 0.26 mmol) was successfully coupled with $GTP_3$ to give Mor-Suc-$GTP_3$ (0.215 g) in 65.6% isolated yield. The product was purified by flash chromatography on alumina with 10% MeOH/EtOAc elution.

By HPLC (System II) both Mor-Suc-$GTP_2$ and Mor-Suc-$GTP_3$ were of high purity and free from parent drug.

EXAMPLE 4

Synthesis of AZT-Gly-Tris-(Palmitate)$_n$; where n=1, 2 or 3.

Synthesis Scheme Overview

AZT was reacted with succinic anhydride to form AZT-succinic acid. This was reacted by the DCC/HOSu method with a mixture of Gly-Tris-Mono, Di and Tripalmitate (GTP$_n$) which was prepared by catalytic hydrogenation of Z-GTP$_n$. Column chromatography on silica gel and preparative HPLC were used to isolate the final compounds:

I. AZT-Succinic Acid

AZT (1.068 g, 4 mmol), succinic anhydride (0.440 g, 4.4 mmol) and DMAP (0.015 g) were weighed into a 25 ml flask fitted with a condenser. DMF (10 ml) was added and the mixture stirred for 5 min and immersed into an oil bath preheated to 90° C. for 1.5 h until HPLC assay indicated completion of reaction. DMF was evaporated under vacuum (<40° C.) and the residue used directly for the subsequent reaction. The residue can be purified by chromatography on silica gel and the product isolated in >87% yield and 97% purity if required.

II. AZT-Suc-Gly-Tris-(Palmitates)$_n$: where n=1, 2 and 3

AZT-Succinic acid (1.468 g, 4 mmol) was dissolved in DCM (30 ml) and HOSu (0.552 g, 4.8 mmol) added. The mixture was stirred for 5 min, then DCC (0.988 g, 4.8 mmol) was added in one portion. Stirring was continued for 1 hr until HPLC analysis indicated completion of the reaction. The reaction mixture was filtered and the insoluble DCU washed with DCM (35 ml). The combined filtrate was collected in a reaction vessel, then GTP$_n$ (2.5 g) added and stirred overnight. The reaction was monitored by HPLC. Extra GTP$_n$ was added until all the active OSu ester was consumed. The reaction mixture was evaporated in vacuo. The product was purified by column chromatography on silica using hexane/ethyl acetate and ethyl acetate/methanol as eluent to separate the AZT-Suc-Gly-Tris Mono, Di and Tripalmitates. The products were further purified by preparative HPLC (C18 column).

EXAMPLE 5

Method One for the Preparation of Cyclosporin-Suc-Gly-Tris-(Palmitate)$_n$; where n=1, 2 or 3.

I. Cyclosporin-Suc

The title compound can be prepared from cyclosporins A, B, D, and G by their reaction with succinic anhydride in the presence of triethylamine in DMF. The threonine side chain in cyclosporin C would require prior protection before carrying out this reaction.

II. Cyclosporin-Suc-Gly-TRIS

The title compound can be prepared by the reaction of cyclosporin-Suc with Gly-Tris in the presence of DCC and HOSu.

III. Cyclosporin-Suc-Gly-TRIS mono, di and tripalmitates

The title compounds can be prepared by the reaction of cyclosporin-Suc-Gly-Tris with palmitic acid at a molar ratio of 1 to 2 in the presence of DCC. The three title compounds can then be separated by preparative HPLC or via silica gel chromatography with elution by organic solvents. With cyclosporin C the side chain protection would be removed prior to purification.

Method Two for the Preparation of Cyclosporin-Suc-Gly-Tris-(Palmitate)$_n$; where n=1, 2 or 3.

I. Preparation of the benzyl ester of Suc-Gly-Tris-TriOTBDMS

Suc-mono benzyl ester can be prepared by the reaction of succinic anhydride with benzyl alcohol in the presence of strong base. The remaining unmodified carboxyl group can then be reacted with Gly-Tris in the presence of DCC and HOSu to give Bzl-Suc-Gly-Tris. The three hydroxyl groups of Tris can then be protected by reaction with TBDMS chloride in the presence of imidazole to give the title compound.

II. Cyclosporin-Suc-Gly-Tris-Mono, Di and Tripalmitates

The benzyl ester of Bzl-Suc-Gly-Tris-TriOTBDMS can be removed using hydrogen in the presence of palladium on carbon to generate an unprotected carboxyl group which can be reacted with the hydroxyl group of cyclosporin (A, B, D, and G; as above side chain protection would be required for cyclosporin C) in the presence of DCC to generate an ester bond. The three TBDMS protected hydroxyls of Tris in this compound can be deprotected by the action of acetic acid and reacted with palmitic acid in the presence of DCC to give a mixture of the title compounds. The three title compounds can then be separated by preparative HPLC or via silica gel chromatography.

EXAMPLE 6

Synthesis of Methotrexate-Gly-Tris-Di and Tripalmitate.

Synthesis Scheme Overview

The method devised involved removal of the glutamyl moiety of methotrexate (MTX) by enzymatic cleavage with Carboxypeptidase G and replacing it with glutamic acid which had its two carboxyl groups selectively esterified (α-tertbutyl; γ-methyl). Selective removal of the methyl ester then provided the site for the attachment of Gly-Tris which was subsequently palmitylated and the dipalmitate derivative (and a small amount of the tripalmitate) were isolated by silica chromatography and/or extraction.

I. [[(2,4-Diamino-6-Pteridinyl)Methyl]Methyl Amino] Benzoic Acid

The title compound was prepared by carboxypeptidase G cleavage of glutamic acid from methotrexate as described in the literature (J. Med. Chem. 24, 1450–1455 (1981)). The yield of I obtained was virtually quantitative.

II. α-tertButyl γ-Methyl L-Glutamate

The title compound was prepared from γ-methyl L-glutamate according to the literature (Justus Liebigs Ann. Chem. 646, 134 (1961)). Yields were highly variable but typically in the 30–50% range. Compound II, obtained as an oil was used immediately in subsequent coupling reactions.

III. α-tertButyl γ-Methyl Methotrexate

The title compound was prepared from I and II according to the literature [J. Med. Chem. 24, 1450–1455, (1981)]. Yields were typically 50–60%.

IV. α-tertButyl Methotrexate

The title compound was prepared by Ba(OH)$_2$ hydrolysis of III according to the literature (J. Med. Chem. 24, 1450–1455 (1981)). Compound IV was typically obtained sufficiently pure not to require purification by ion exchange chromatography as evidenced by $^1$H NMR. Yields were typically in the 75–80% range.

V. Methotrexate-α-tertButyl γ-Gly-Tris

To IV (100 mg, 0.20 mmol) in DMF/acetonitrile (1:1, 6 ml) was added HOSu (21 mg, 0.22 mmol) followed by DCC (45 mg, 0.22 mmol). The reaction mixture was stirred at room temperature and monitored by HPLC (System I). Preparation of the OSu ester was >85% complete after 5 h with HPLC analysis indicating the remainder to be IV along with some decomposition products. A solution of Gly-Tris (prepared by hydrogenation of Z-Gly Tris in DMF over 10% Pd/C (1.5 eq. in 3 ml DMF)) was added and the reaction followed by HPLC. The reaction was complete within 30–60 min. The reaction mixture was then diluted with H$_2$O (3–5 ml), allowed to stand for 10 min and the DCU filtered off. Solvent was removed from the filtrate, and the residue purified via preparative HPLC to afford the title compound as a bright yellow solid after removal of solvent by freeze drying. Yield—30 mg, 23%. On a larger scale using 800 mg of IV a 69% yield of V was obtained. HPLC indicated the purity of the product to be >97%.

VI. Methotrexate α-tertButyl Ester γ-Gly-Tris (palmitate)$_n$; where n=2 or 3

To a suspension of V (650 mg, 0.97 mmol) in DCM (50 ml) was added sufficient DMF to affect solubilisation (5–10 ml), followed by DMAP (30 mg), palmitic acid (500 mg, 2 eq.) and DCC (400 mg, 2 eq.). The mixture was stirred at RT for 36 hrs after which time it was diluted with DCM (80 ml) and chilled in ice for 10 min. The mixture was filtered and the filtrate extracted with 0.01M HCl (100 ml) followed by brine (2×100 ml). After drying (MgSO$_4$) and removal of solvent, the residue was applied to a silica column and eluted consequently with DCM, DCM/5% MeOH, DCM/10% MeOH which afforded the Tri and Dipalmitates of VI as yellow bands which bled off the column. Fractions which were pure by TLC (DCM/isopropanol(30%)) were combined and solvent removed to afford the title compounds as bright yellow solids.

VII. Methotrexate-γ-Gly-Tris-Dipalmitate

To VI (200 mg, 0.17 mmol) was added TFA (5 ml). The mixture was stirred at RT for 20–30 min upon which time solvent was removed by evaporation. The residue was partitioned between DCM (50 ml) and H$_2$O (50 ml), TEA was added to the aqueous phase until the pH was >7. Upon this time acetic acid was added until the pH reached 3–4. The organic phase was collected and washed with H$_2$O (50 ml). dried (Na$_2$SO$_4$) and solvent removed. The product, which was pure by TLC (butanol/acetic acid/water, 4:2:1), was washed with ethanol and dried to afford the title product as a golden solid.

EXAMPLE 7

Synthesis of L-DOPA-Gly-Tris-(palmitate)$_n$; where n=1, 2 or 3.

Synthesis Scheme Overview

The two phenolic hydroxyl groups of DOPA, as well as the amino group were protected and the active ester of Z$_3$-DOPA prepared. The formation of active ester of the fully protected compound was best using TPTU probably due to the structurally hindered nature of this compound. This was reacted with Gly-Tris-Dipalmitate to give Z$_3$-DOPA-Gly-Tris-Dipalmitate.

An alternative synthesis was by palmitylation of Z$_3$-DOPA-Gly-Tris (prepared from Z$_3$-DOPA and Gly-Tris via the active ester method). Hydrogenation of these products yielded the desired DOPA-Gly-Tris-Dipalmitate and DOPA-Gly-Tris-Tripalmitate in good yields.

I. N,O'O'-Tricarbobenzoxy-L-DOPA (Z$_3$-Dopa)

The method for the preparation of Z$_3$-DOPA was that of Felix et al. 1974 (J. Med. Chem. 17, 422–426). The title compound was synthesised by adding L-DOPA (7 g, 35.5 mmol) to a pre-cooled solution of 1M NaOH (35.5 ml) and water (74 ml) at −10° C. under a blanket of nitrogen in a 3-neck flask. The solution was stirred vigorously, whilst 1M NaOH (100 ml) and a solution of carbobenzoxy chloride (20.2 g, 116.5 mmol) in diethyl ether (100 ml) were added dropwise, simultaneously, over a period of 1 h at −10° C. Stirring was continued at −10° C. for 1 h, then 1 h at 0° C. and finally at 20° C. for 2 h. The precipitated sodium salts were collected by filtration, washed with diethyl, ether and water and partitioned between diethyl ether and 1M citric acid (100 ml each). The ether layer was washed with water, dried (Na$_2$SO$_4$) and the solvent removed in vacuo to give the crude title product as an oil (18 g, 84.6% yield).

Further purification of the title product by preparative HPLC (Reverse phase C18 column) gave chromatographically pure title product, R$_t$II 4.77'.

II. Z$_3$-DOPA-Gly-Tris-Dipalmitate

The active ester of Z$_3$-DOPA was prepared by adding a solution of TPTU (1.68 g, 5.62 mmol) in acetonitrile (30 ml) to a stirred solution of Z$_3$-DOPA (1.68 g, 2.8 mmol) in acetonitrile (20 ml) and DIEA (550 ul to pH 8.50). The reaction was followed by HPLC and monitored at 300 nm. After 10 min the reaction was complete and the solvent and base evaporated in vacuo. The residue was redissolved in DCM, re-evaporated, and the procedure repeated twice to ensure the complete removal of base. A solution of the residue in DCM (30 ml) was added to a stirred solution of GTP$_2$ (2.0 g, 3 mmol) in DCM (15 ml) in an atmosphere of nitrogen in the dark.

HPLC, monitored at 260 nm. showed, that the reaction was complete in 30 min to give a single product. The reaction mixture was diluted with DCM (120 ml), washed with water (3×120 ml) and dried (Na$_2$SO$_4$). The DCM layer contained the desired title product which gave a single peak on HPLC (R$_t$II 8.70'). The solvent was removed in vacuo and the residue repeatedly washed with cold acetonitrile to give the title product as a white fluffy precipitate, 3.40 g, in 98% yield. HPLC, TLC and NMR spectroscopy showed that the title product was of high purity.

Hydrogenation of an aliquot of the above product in ethanol in the presence of catalytic amounts of 10% palladium on carbon for 5 h gave L-DOPA-GTP$_2$, R$_t$II 8.05' with an absorption max at 285 nm. Yield was 785 mg, 83.5%.

Analysis by HPLC indicated that the title product was 99% pure, free from the parent drug.

III. Preparation of Z$_3$-DOPA-Gly-Tris

A solution of Z$_3$-DOPA (800 mg, 1.33 mmol) in dry acetonitrile (10 ml) was reacted with a solution of TPTU (1 g, 3.4 mmol) in acetonitrile (5 ml) and DIEA (350 ul, to pH 8.3) and the formation of active ester monitored by HPLC in System II at 300 nm. The reaction was complete in 10 min to give the active ester in 89% yield by HPLC, R$_t$II 5.19'. Repeated evaporation of the solvent and DIEA from DCM gave an oily residue, which was redissolved in acetonitrile (15 ml) and added dropwise to a solution of Gly-Tris (1 g, 5.6 mmol) in freshly distilled, dry DMF (5 ml) with stirring. The reaction was monitored by HPLC at 300 nm and at 260 nm which showed the formation of the title product in both HPLC systems, I and II (Rt 7.11' and 3.05' respectively).

The solvents were removed in vacuo and the title product purified by preparative HPLC to give 655 mg of Z$_3$-DOPA-Gly-Tris (60.4% yield). The structure of the product was confirmed by NMR Spectroscopy.

IV. Z$_3$-DOPA-Gly-Tris-Di and Tripalmitate

A solution of Z$_3$-DOPA-Gly-Tris (600 mg, 1 mmol) in DCM (10 ml) as reacted with palmitic acid (312 mg, 1.22 mmol) and DCC (250 mg, 1.2 mmol) as described above. The reaction was followed by HPLC with additional palmitic acid added in 10 mg aliquots as required. After addition of a further 40 mg of palmitic acid, Z$_3$-DOPA-Gly-Tris-Mono and Dipalmitate were formed in a 1:1 ratio as determined by HPLC. After removal of DCU by filtration, the solvent was removed in vacuo and the mixture separated by preparative HPLC using a C18 column.

During the workup procedure, most of the product converted to the Di- and the Tripalmitate forms, which were separated to give 260 mg of dipalmitate and 520 mg of tripalmitate, calculated on the percentages shown by HPLC traces of the mixture (21% P$_2$; 35% P$_3$).

L-DOPA-GTP$_2$ and GTP$_3$ were obtained by hydrogenation in ethanol in the presence of Pd/C catalyst to give the desired title products.

EXAMPLE 8

Synthesis of Chlorambucil-Gly-Tris-(Palmitate)$_n$; where n=1, 2 or 3.

The title compounds were formed by preparing the active ester of chlorambucil and reacting this with a mixture of Gly-Tris Mono, Di and Tripalmitate (GTP$_n$) produced by hydrogenation of Z-GTP$_n$. The resulting products were purified by column chromatography and preparative HPLC.

I. Chlorambucil-Gly-Tris-(Palmitate)$_n$; where n=1, 2 or 3

Chlorambucil (0.913 g, 3 mmol) and HOSu (414 mg, 3.6 mmol) were weighed into a 50 ml flask with a magnetic stirring bar. DCM (15 ml) was added and the solution stirred for 5 min. DCC (742 mg, 3.6 mmol) in DCM (15 ml) was added within 5 minutes. Analytical HPLC indicated completion of reaction after 1 h.

The solution was filtered and the residue rinsed with DCM (10 ml). The combined filtrate was collected in a flask, stirred and solid GTP$_n$ (4 g) added. Stirring was continued overnight and fresh GTP$_n$ added (300 mg). HPLC after 2 h showed the absence of the chlorambucil-OSu ester indicating the completion of the reaction.

The mixture was evaporated under vacuum (<40° C.). The product was chromatographed over silica gel using hexane-:ethyl acetate followed by preparative HPLC to generate high purity products.

II. Chlorambucil-Gly-Tris-Monopalmitate

To a solution of chlorambucil (0.972, 3.2 mmol) in DCM (32 ml) was added DCC (0.726 g, 3.5 mmol) and HOSu (0.387 g, 3.3 mmol) portionwise at 0° C. The resulting mixture was stirred at room temperature overnight. After the completion of the reaction according to HPLC (System I), the precipitate (DCU) was filtered and washed with dry DCM (10 ml). To the filtrate was added Gly-Tris-Monopalmitate (1.208 g, 2.9 mmol) portionwise with vigorously stirring at rt overnight. When the reaction was completed, the resulting mixture was diluted with DCM, then washed with H$_2$O several times. The organic phase was dried (MgSO$_4$) and evaporated in vacuo to afford the crude product. The crude product was purified by the flash chromatography (80% ethyl acetate/hexane, 2.5% MeOH/ethyl acetate) to give the title compound (0.950 g) as light yellow semi solid in 46.6% yield.

III. Chlorambucil-Gly-Tris-Tripalmitate

To a solution of chlorambucil (0.240 g, 0.789 mmol) in DCM (16 ml) at 0° C. was added DCC (0.171 g, 0.828 mmol) and DMAP (0.005 g, 0.039 mmol), followed by the Gly-Tris-Tripalmitate (0.740 g, 0.828 mmol). The resulting mixture was stirred at room temperature overnight. The precipitate was filtered and the filtrate washed with 5% acetic acid aqueous solution, then H$_2$O three times until the pH was 7. The organic phase was dried (MgSO$_4$), then concentrated in vacuo. The crude product was purified by the flash chromatography (30%, 40% ethyl acetate/hexane), then recrystallized from ethyl acetate/hexane to give the title compound (0.45 g) as a white solid in 48.2% yield.

EXAMPLE 9

Anti-inflammatory Effect of Hydrocortisone and Hydrocortisone Fatty Acid Conjugates in the UVB Model

Drugs Used

Hydrocortisone was purchased from Sigma Chemicals, Lot no. 13H0525. H-4001. Hydrocortisone-Suc-GTP$_2$, and Hydrocortisone-Suc-GTP$_3$ and 17b Hydrocortisone Suc-GTP$_3$ were synthesised as described above.

UVB Erythema Assay

A strain of i/b Skh-1 hairless albino female mice not previously exposed to UVB were used in all experiments. The average age was 12 weeks and the mice were boxed in groups of three (Average weight 30 g). An FS40 light source with one UVB tube was used to induce the erythema (inflammation). The mice were exposed to 15 minutes of UVB equivalent to an exposure of 2MED (minimum erythema dose). The irradiated mice were given either a post-irradiation treatment or were pretreated several days prior to UVB exposure by evenly dispersing 100 μls of a solution of the Hydrocortisone, Hydrocortisone-Suc-GTP$_2$, or Hydrocortisone-Suc-GTP$_3$, in ethanol (vehicle), onto the backs of mice using a Gilson pipettor. The mice were left for 24 hours and the skin fold measurements taken using a hand held micrometer.

Experimental

As an initial part of the study we examined the effect of Hydrocortisone on UVB induced inflammation. A group of Skh-1 mice were irradiated with 2MED of UVB and then painted topically with Hydrocortisone in ethanol. The net skin fold thickness increase (NSFT) was determined after 24 h. The concentration curve carried out determined the optimal dose of Hydrocortisone required to give the best anti-inflammatory protection from an exposure of 2 MED of UVB. A dose of 0.5 mg/mouse gave almost 100% protection from erythema and oedema, this was used in subsequent experiments examining the effects of Hydrocortisone conjugates.

Hydrocortisone-Succinate Fatty Acid Conjugates and their Protection against UVB Induced Oedema The longevity of topically applied Hydrocortisone-Succinate fatty acid conjugates was examined. Hydrocortisone concentrations of 0.5% and 1% w/v were used (equivalent to 0.5 mg and 1.0 mg/mouse respectively) and the results are presented below. The test conjugates were applied 5 and 3 days prior to UV exposure. At day 0 the conjugates were applied after UV exposure to avoid the possibility of TV absorption (sunscreen effect).

Results of the 0.5 mg/mouse experiments are given in Table 1.

TABLE 1

Mean Net Skin Fold Thickness (10$^{-2}$ mm) Measurements for 0.5 mg/mouse Hydrocortisone and Conjugates (HC-Suc-GTP$_2$ and GTP$_3$ and 17-b HC-Suc-GTP$_3$)

| Drug | Day −5 | Day −3 | Day 0 |
| --- | --- | --- | --- |
| 0.5 mg/mouse Hydrocortisone | 102.7 ± 12.1 | 100.9 ± 7.3 | 10.4 ± 8.19 |
| 0.5 mg/mouse HC-Suc-GTP$_2$* | 104.2 ± 14.7 | 94.3 ± 10.3 | 60.6 ± 8.6 |
| 0.5 mg/mouse HC-Suc-GTP$_3$* | 93.8 ± 9.8 | 86.7 ± 9.4 | 55.8 ± 11.7 |
| 0.5 mg/mouse 17-b HC-Suc-GTP$_3$ | | 90.7 ± 14.8 | 42.7 ± 13.7 |
| Vehicle | | | 112.6 ± 10.4 |

*0.5 mg with respect to HC content.

Results

The three forms of the Hydrocortisone-succinate conjugates, Hydrocortisone-Suc-Gly-Tris-Dipalmitate (HC-Suc-GTP$_2$), Hydrocortisone-Suc-Gly-Tris-Tripalmitate (HC-Suc-GTP$_3$) and 17-b HC-Suc-GTP$_3$ had activity equivalent to approximately 50% of the hydrocortisone activity in protecting against UVB induced oedema when applied at Day 0, post UVB exposure. It was also observed that when the conjugates were applied to the mouse skin three days before UVB exposure there was still a protective effect present with both conjugates and this appeared to be slightly better than Hydrocortisone alone. There was a smoothing (delay) of the response with the conjugates indicating an altered delivery profile.

At the higher concentration of 1 mg/mouse the protective effects of the Hydrocortisone conjugates was enhanced (Table 2) with greater protection with all test compounds at Day-3. Once again there was a delay in the action of the hydrocortisone conjugates suggesting a more sustained, even delivery profile.

TABLE 2

Mean Net Skin Fold Thickness Measurements for 1% w/v Hydrocortisone and Conjugates

| Drug | Day −5 | Day −3 | Day 0 |
|---|---|---|---|
| 1 mg/mouse Hydrocortisone | 108.3 ± 5.1 | 62.9 ± 4.0 | 7.9 ± 4.4 |
| 1 mg/mouse HC-Suc-GTP$_2$* | | 60.8 ± 8.8 | 57.5 ± 10.9 |
| 1 mg/mouse HC-Suc-GTP$_3$* | 103.8 ± 3.0 | 62.9 ± 4.0 | 27.9 ± 7.5 |
| Vehicle | | | 114.0 ± 8.0 |

*with respect to HC content.

Conclusions

The efficacy of Hydrocortisone-succinate fatty acid conjugates was determined in a mouse UVB model of inflammation. The overall biological findings are that the fatty acid conjugated forms of Hydrocortisone synthesised are similar to Hydrocortisone in their biological action as measured by their protection against UVB induced erythema and oedema. Importantly, the fatty acid conjugates appear to have an altered profile of delivery to the epidermis, suggested by the delay in full activity at Day 0.

The results indicate that there may be some advantage in using fatty acid conjugated molecules over Hydrocortisone in respect to improved compartmentalisation with transdermal delivery. This altered delivery may also reduce the side effects brought about by the down regulation of the H-P-A axis through prolonged use of Hydrocortisone.

EXAMPLE 10

Contact Hypersensitivity Assay

The assay used the method described in "Current Protocols in Immunology" (Vol 1, Section 4.2 Eds Coligan et al. (1991) NIH). The sensitiser was Oxazalone. Briefly this method was as follows:

UVB Radiation. Mice were irradiated with a single FL40SE UVB fluorescent tube (Oliphant) in a reflective batten, providing $2.6 \times 10^4$ W/cm$^2$ UVB radiation measured at target distance using an International Light IL1700 radiometer with a UVB detector sensitive between 250–315 nm. The mice received 0.1179 J/cm$^2$ UVB radiation, constituting 1 minimal erythemal dose (MED) as previously ascertained, on each of 3 consecutive days, being exposed unrestrained with the wire cage tops removed. The cumulative dose resulted in a moderate non-blistering erythema. The erythema was quantitated as the oedema component of this reaction by measuring the mid-dorsal skinfold thickness with a spring micrometer (Mercer, St. Albans, UK) at 24 h after the first UVB exposure, i.e. immediately prior to the third UVB exposure, at which time the reaction was found to be maximal.

Induction of Systemic Contact Hypersensitivity. Test mice were exposed on the dorsum to 1 MED UVB radiation (or no UVB radiation) at the same hour on days 1, 2 and 3. On days 8 and 9, the mice (irradiated and non-irradiated) were sensitized by topical application to the abdominal skin of 0.1 ml of 3% (w/v) oxazolone (Sigma Chemical Co., St Louis, Mo.) freshly prepared in ethanol. On day 15, the pre-challenge ear thickness was measured using the spring micrometer, and the mice were then challenged by the application of 5 ul freshly prepared 3% oxazolone/ethanol solution to both surfaces of each pinna. Ear thickness was again measured repeatedly between 16–24 hours, and the maximum ear thickness was recorded. The net ear swelling was calculated as the difference between the average pre-challenge and the average post-challenge ear thickness for each treatment group. Statistical significance of the differences in net ear swelling between treatment groups was assessed with Student's t test.

The mice were painted with vehicle, 0.5 mg/mouse HC, 0.5 mg/mouse HC-Suc-GTP$_2$. 1 mg/mouse 17-b HC-Suc-GTP$_3$ or 17-b HC within 10 minutes post UVB exposure. A total of 3 MED of unshielded UVB was used. (Table 3)

TABLE 3

Contact Hypersensitivity Results

| Test Material | Net Ear Swelling (10$^{-2}$ mm) | Std. Dev. |
|---|---|---|
| Vehicle Control | 17.7 | 6.94 |
| 0.5% HC-Suc-GTP$_2$ | 29.8 | 5.05 |
| 0.5% Hydrocortisone | 32.0 | 9.30 |
| 1% 17b-Hydrocortisone | 38.6 | 4.41 |
| 1% 17b-HC-Suc-GTP$_3$ | 32.8 | 10.28 |
| No UVB Control | 42.1 | 6.08 |

Results

All the samples tested showed protection against the UVB induced immunosuppression indicated by an increase in ear thickness as the result of a systemic response to the sensitiser. There appeared to be no difference between the parent drugs or the conjugates in their ability to alter the immunosuppression due to UVB. Importantly however is that the conjugates appear to be just as active as the parent drugs in producing a systemic response.

EXAMPLE 11

AZT

The biological activities of AZT and AZT-fatty acid conjugates were tested for cytotoxicity and anti-HIV activity.

I. Cytotoxicity

The cytotoxicity of AZT and AZT-fatty acid conjugates (AZT-Suc-GTP$_1$, P$_2$ and P$_3$) was tested in vitro with JURKAT (acute T cell human leukemia) and peripheral blood mononuclear cells (PBMC). Cells were incubated with drug and viability was determined by a calorimetric proliferation test.

Methods a) Cell Culture Conditions

JURKAT cells were seeded into 96-well plates at a density of $1.6 \times 10^4$ cells/200 ul complete RPMI 1640 medium±drug and cultured for 64 h.

Human peripheral blood mononuclear cells (PBMC) were isolated from three healthy donors by centrifugation on Ficoll-Paque (Pharmacia). Cells were seeded into a 96-well plates at a density of $2 \times 10^5$ cells/200 ul complete RPMI±drug and cultured for 40 h.

b) Drug Delivery

Drugs were dissolved in ethanol and added to culture media. The final concentration of ethanol in media was no greater than 1% (v/v).

c) Viability Assay

Viability was determined using the MTS assay (CellTiter 96TM AQueous Non-Radioactive Cell Proliferation Assay) from Promega. Reagent (40 ul) was added to each well and absorbance values at 490 nm were determined 1 to 4 h later. The effect of drug on cell viability was compared to cultures set up containing no drug (100% viability). Wells containing no cells were used to control for background absorbance (0% viability). Each concentration was tested in at least 3 wells. Concentrations necessary to cause a 50% inhibition of cellular growth of control cells (IC50) were calculated by linear regression.

Results

AZT-Suc-GTP$_1$ was 40 times more cytotoxic to JURKAT cells than the parent drug (Table 4). The conjugate was also more cytotoxic to PBMC than AZT.

TABLE 4

Cytotoxicity of AZT and AZT-Suc-GTP$_1$ to PBMC and JURKAT cells

| Cell Type | Compound | IC$_{50}$ (uM) |
|---|---|---|
| JURKAT | AZT | 1720.8 |
|  | AZT-Suc-GTP$_1$ | 43.0 |
| PBMC | AZT | >105 |
|  | AZT-Suc-GTP$_1$ | 26.7 |

II. Anti HIV Activity

The anti-HIV activities of AZT-Suc-GTP$_1$ and AZT-Suc-GTP$_2$ were also tested. Infected cells were incubated for 5 days with compound. Compounds were dissolved in DMSO and 5-fold dilutions were used. The following parameters were measured: syncytia formation, virus antigen gp120 production, cell survival. Cytotoxicity is also measured in uninfected cells.

Two cell lines were used:

C8166 (human T-lymphoblastoid cells) infected with HIV-I MN

JM (semi mature human T-cell from lymphoblastoid leukemia) infected with HIV-I U4550

AZT is poorly active in JM cells possibly due to insufficient phosphorylation and was used to confirm the mode of action of compounds.

Results

TABLE 5

Effect of AZT-Suc-GTP$_1$, AZT-Suc-GTP$_2$, AZT and ddI on cellular growth and HIV infection (Ag gp120 production) in JM and C8166 cells

|  | JM | | C8166 | |
|---|---|---|---|---|
| Compound | EC50 | IC50 | EC50 | IC50 |
| AZT-Suc-GTP$_1$ | 8 μM | 100 μM | 0.012 μM | 100 μM |
| AZT-Suc-GTP$_2$ | >200 μM | 200 μM | 0.032 μM | 200 μM |
| AZT | 100 μM | 5000 μM | 0.016 μM | 5000 μM |
| ddI | 1 μM | >100 μM | | |

EC50 = concentration which reduces Ag gp120 by 50% in infected cell cultures.
IC50 = concentration of drug which reduces cell growth by 50%.

The AZT-Suc-GTP$_1$ conjugate was 50-fold more cytotoxic to both cell lines than AZT (Table 5); this is consistent with the findings with PBMC and JURKAT cells (Table 4). Cytotoxicity of the P$_2$ conjugate was also observed with JM and C8166 cells (25-fold more cytotoxic than AZT).

TABLE 6

Ratios of AZT: Conjugate EC50 (Data from Table 5)

| Cell Line | AZT:AZT-Suc-GTP$_1$ | AZT:AZT-Suc-GTP$_2$ |
|---|---|---|
| JM | 12.5 | approx. 0.5 |
| C8166 | 1.3 | 0.5 |

The virus in the JM cell line was 12.5-fold more susceptible to AZT-Suc-GTP$_1$ than AZT (Table 6). This increase in toxicity towards the virus was not reflected in the pattern of HIV infection: syncytia formation or infected cell growth profiles; the effect is only observed with the detection of antigen. The JM cell line does not metabolise AZT to the same extent as C8166 cells but greater delivery of AZT via the P$_1$ conjugate may result in higher levels of the triphosphate being formed in the cells.

Discussion

AZT-Suc-GTP$_1$ was more cytotoxic than AZT to PBMC, JURKAT, C8166 and JM cells suggesting increased cellular uptake. Cellular kinases convert AZT to AZT-triphosphate, which inhibits HIV reverse transcriptase (RT) and at 100-fold higher concentrations inhibits cellular α-DNA polymerase. It appears that conjugation increases cell uptake, thus increasing cytoxicity (Table 5). In infected JM cells, AZT-Suc-GTP$_1$ was more potent in reducing amounts of Ag gp 120 produced by HIV, however because of the cytotoxic nature of this compound cells did not recover and exhibit normal growth.

These are very positive results in that they are consistent with the conjugates being taken up by the cells and being metabolised to release AZT to act in the usual manner. Their cytotoxicity (which may have beneficial effects if targeted), while above that of unmodified AZT, is at a low enough level to allow their use.

These findings may allow some of the major limitations of current AZT therapy, namely its rapid clearance, poor bioavailability and its poor delivery to the lymphatic system which is the primary site of virus load, to be addressed. Quoting Charman and Porter (1996 Advanced Drug Delivery Reviews in press) "the major opportunities associated with lipophilic prodrugs are the potential for (i) by-passing hepatic first pass metabolism after oral dosing, and (ii)

targeting drugs to the lymphatic system." Additionally the lipophilic prodrug such as our AZT-Suc-GTP$_1$ should act to give a sustained release profile. These features should result in lower overall doses of AZT being required with the possibility of lessened side effects in spite of the overall general more cytotoxic nature of the conjugates compare with AZT.

EXAMPLE 12

CHLORAMBUCIL

The cytotoxicity of chlorambucil and chlorambucil fatty acid conjugates (CGTP$_1$, P$_2$ and P$_3$) were tested in vitro with JURKAT cells (acute T cell human leukemia). Cells were incubated with drug and viability was determined by a colourmetric proliferation test. Cytotoxicity towards other cells lines was also tested (PC3 human prostate cancer cells, B16 mouse melanoma cells and human peripheral blood mononuclear cells).

Methods a) Cell Culture Conditions

JURKAT cells were seeded into 96-well plates at a density of $1.6 \times 10^4$ cells /200 µl complete RPMI±drug and cultured for 64 h. A 1:3 split of confluent PC3 cells in a 75 cm$^2$ flask were seeded into a 96-well plate and cultured for 48 h in complete RPMI. Media was removed and complete RPMI±drug was added to wells. Cells were further cultured for 72 h.

A 1:8 split of confluent B16 cells in a 75 cm$^2$ flask were seeded into a 96-well plate and cultured for 48 h in complete EMEM. Media was removed and complete EMEM±drug was added to wells. Cells were further cultured for 48 h.

Human peripheral blood mononuclear cells (PBMC) were isolated from one healthy donor by centrifugation on Ficoll-Paque (Pharmacia). Cells were seeded into a 96-well plates at a density of $2 \times 10^5$ cells/200 µl complete RPMI±drug and cultured for 40 h.

b) Drug Delivery

Two types of delivery were tested:

i) Ethanol. Drugs were dissolved in ethanol and added to culture media. The final concentration of ethanol in media was no greater than 1% (v/v). This delivery was used for experiments with JURKAT, PBMC, PC3 and B16 cell types.

ii) Coating of plates. Drugs were dissolved in ethanol and aliquots (up to 40 ul) were added to 90% (v/v) isopropanol. Solution (50 ul) was then added to wells of a 96-well plate and the solvent evaporated by heating at 37° C. Media±cells was then added. This delivery was used for some experiments with JURKAT cells.

c) Viability Assay

Viability was determined using the MTS assay (CellTiter 96TM AQueous Non-Radioactive Cell Proliferation Assay) from Promega. Reagent (40 ul) was added to each well and absorbance values at 490 nm were determined 1 to 4 h later. The effect of drug on cell viability was compared to cultures set up containing no drug (100% viability). Wells containing no cells were used to control for background absorbance (0% viability). Each concentration was tested in at least 3 wells. Concentrations necessary to cause a 50% inhibition of cellular growth of control cells (IC50) were calculated by linear regression.

Results a) Drug Cytotoxicity

CGTP$_1$ was more cytotoxic to all cell type s tested than chlorambucil (Table 7).

TABLE 7

Concentrations of Chlorambucil and CGTP$_1$ necessary to cause a 50% inhibition of the cellular growth of control cells (IC50) in different cell types

| | IC50 | | |
|---|---|---|---|
| Cell Type | Chlorambucil (uM) | CGTP$_1$ (uM) | Chlorambucil to CGTP$_1$ Ratio |
| JURKAT | 100.6 | 6.5 | 15.5 |
| PC3 | 160.2 | 10.7 | 15.0 |
| B16 | 36.5 | 23.1 | 1.6 |
| PBMC (1) | 45.0 | 7.1 | 6.3 |
| PBMC (3) | <22 | 5.5 | approx. 4 |

() = number of donors from which PBMC isolated.

A 15-fold increase in activity was observed with JURKAT cells. The increase in toxicity of CGTP$_1$ to normal cells (PBMC) was not as great (approximately 5-fold). JURKAT cells appear to be more resistant to chlorambucil than PBMC. CGTP$_1$ is cytotoxic to both cell types at similar concentrations. The GTP$_1$ conjugate was also more toxic to PC3 and B16 cell types.

CGTP$_1$ was more cytotoxic to JURKAT cells than an equimolar mixture of chlorambucil and GTP$_1$. GTP$_1$ had no activity. This indicates that conjugation of chlorambucil to GTP$_1$ is necessary for the increased cytotoxicity observed (Tables 7, 8, 9).

b) Effect of Vehicle

Both vehicles (ethanol & isopropanol) were not cytotoxic to cells in the dose range studied. Delivery of compounds by coating the plates increased IC50 values of chlorambucil and CGTP$_1$ (Table 8), however this method of delivery detected activity with CGTP$_2$ and CGTP$_3$ (Table 9) which was not observed when these compounds were delivered to cultures in ethanol. This effect may be due to the reduced solubility of the P2 and P$_3$ conjugates in the aqueous in vitro tests.

TABLE 8

Comparison of IC50 values of Chlorambucil and CGTP$_1$ delivered to JURKAT cells by coating of plates and addition of ethanol solution to culture media

| | IC50 (uM) | |
|---|---|---|
| Compound | ethanol | coated |
| Chlorambucil | 100.6 | 218.6 |
| CGTP$_1$ | 6.5 | 8.6 |

TABLE 9

Cytotoxicity of Chlorambucil and fatty acid conjugates to JURKAT cells. Drugs were coated onto plates.

| Compound | IC50 (uM) |
|---|---|
| CGTP$_1$ | 8.4 |
| CGTP$_2$ | 17.7 |
| CGTP$_3$ | 30.0 |
| Chlorambucil | 218.7 |

Discussion

Increased biological activity of the PI conjugate of chlorambucil was demonstrated with a variety of cell types.

CGTP$_2$ and CGTP$_3$ also showed improved cytotoxicity towards JURKAT cells.

EXAMPLE 13

MORPHINE

The biological activities of Morphine (Mo) and fatty acid conjugates were tested in an antinociceptive assay using mice. Various doses and duration of pain-killing effect of the drugs were examined.

Methods

Quackenbush Strain mice (male, 5-week-old, approximately 30 g live weight) were used for the experiments. Animals were given free access to food and water prior to and during the experiment. Animals were divided into groups of 12 and individually weighed. The mean weight for each group was calculated. Mice were then placed on a metal block heated to 50° C. and the time taken for the animals to show signs of discomfort was measured (baseline response; control). Mice were then injected intraperitoneally (ip) with various doses of Morphine or Morphine-fatty acid conjugate. Morphine was made up in a H$_2$O solution and Morphine-fatty acids were made up in an emulsion containing 10% glycerylmonooleate, 21% Miglyol, 6% ethanol, 24% Tween 80 (33%) and 39% H$_2$O. 0.2 ml of appropriate solution was injected ip into each mouse. At different times after injection, responses on the heated plate were measured. In each experiment 3 doses of Morphine and Morphine-fatty acid and 2 time points were tested. A single mouse was used for each treatment and the entire experiment repeated at least 3 times. All responses of the animals were filmed, and in some cases mice behaviour was assessed by an independent panel who did not know what treatment the mice had received. Members of the panel were asked to score mice behaviour according to the following key:

0=agitated mouse, distressed

1=showing mild discomfort

2=not agitated or uncomfortable but still alert

3=placid, docile; not at all worried.

Results from the panel were averaged.

Coordination of mice after treatment was also assessed by placing treated animals on a Rotor-Rod at 1.6 rpm. The ability of animals to stay on the rod was assessed.

Results

Experiment 1. Effect of Morphine and Morphine-Suc-GTP$_2$ (5, 10 & 20 mg Morphine/kg) on mice at 1 and 4 hr after injection.

Four replicates of this experiment were analysed by an analysis of variance. There was not significant difference between the different doses examined within drugs. However, when the results of the different doses of each drug were pooled, differences were found (Table 10).

TABLE 10

Time responses and behaviour scores of mice 1 and 4 hr after ip injection of Morphine or Morphine-Suc-GTP$_2$. Results presented are the mean ± SEM, 12 mice in each group.

| Compound | Time Response ± SEM (sec) | | Behaviour Score ± SEM | |
|---|---|---|---|---|
|  | 1 hr | 4 hr | 1 hr | 4 hr |
| Morphine | 32.7 ± 2.74 | 28.2 ± 2.74 | 2.46 ± 0.166 | 1.93 ± 0.166 |
| Morphine-Suc-GTP$_2$ | 26.7 ± 2.74 | 31.2 ± 2.74 | 2.34 ± 0.166 | 2.35 ± 0.156 |

Results were analysed by an analysis of variance.
p = 0.13 for the time responses; p = 0.11 for the behaviour scores.

Both the time response and behaviour score data shows that Morphine-Suc-GTP$_2$ is having a longer lasting pain-killing effect than unconjugated morphine. Mice treated with Morphine-Suc-GTP$_2$ were also tested for coordination. At 1 and 4 hr after injection they were able to stay on the rotor-rod, as were morphine treated animals. This indicates that Morphine-Suc-GTP$_2$ does not affect the coordination of the test animals and is producing a true pain-killing effect.

Experiment 2. Time Course of Morphine and Morphine-Suc-GTP$_2$ activity at 5 mg Mo/kg.

A slow release of Morphine from Morphine-Suc-GTP$_2$ is indicated as there is little activity 1 hr after injection but an increase at 4 and 6 hr (Table 11). Morphine shows maximal activity at 1 hr and decreased with time.

TABLE 11

Mean time response of mice 1, 4 and 6 after ip injection of morphine or Morphine-Suc-GTP$_2$ (5 mg Mo/kg)

| Time | Mean Time Response (sec) | |
|---|---|---|
| (hr) | Morphine | Mo-Suc-GTP$_2$ |
| 1 | 27.8 (4) | 24.0 (4) |
| 4 | 23.9 (8) | 30.5 (8) |
| 6 | 20.0 (4) | 27.8 (4) |

(n) = number of replicates

Experiment 3. Effect of morphine and Mo-Suc-GTP$_3$ (1 and 10 mg Mo/kg) on mice at 4 and 6 hr after injection.

Mo-Suc-GTP$_3$ also displays a longer lasting effect than morphine (Table 12)

TABLE 12

Mean time responses of mice 4 and 6 hr after ip injection of morphine or Mo-Suc-GTP$_3$.
Results presented are the mean time response (sec) and 4 replicates of the experiment were performed.

| Dose | Morphine | | Mo-Suc-GTP$_3$ | |
|---|---|---|---|---|
| mg Mo/kg | 4 hr | 6 hr | 4 hr | 6 hr |
| 1 | 23.2 | 20.8 | 23.5 | 27.8 |
| 10 | 23.0 | 24.2 | 29.8 | 29.0 |

Standard error of each mean = ±2.86

Discussion

The conjugation of Morphine to GTP$_2$ allowed pain-killing activity and did not affect gross motor activity in mice. Morphine-GTP$_2$ has a slow-release delivery profile and a longer lasting pain-killing effect than the parent drug, morphine. Morphine-Suc-GTP$_3$ displayed a similar effect.

EXAMPLE 14

L-DOPA

The biological activities of L-DOPA and L-DOPA-GTP$_2$ were tested in an animal model of Parkinsons' disease, a condition caused by low levels of the neurotransmitter dopamine in the brain. Mice were pretreated with reserpine which depletes dopamine and causes animals to become catatonic. The ability of L-DOPA and L-DOPA-GTP$_2$ to reverse this condition was measured.

Methods

Quackenbush Strain mice (male, 5-week-old, approximately 30 g live weight) were used for the experiments. Animals were given free access to food and water prior to and during the experiment. Mice were injected intraperitoneally (ip) with reserpine (5 mg/kg) and 4 hours later tested for catatonia. A mouse was judged to be catatonic if it was able to stay on a stopper of 4.5 cm diameter for 5 minutes. Catatonic animals were then injected ip with L-DOPA or L-DOPA-GTP$_2$ suspended in Miglyol (200–400 ul/mouse) immediately before use and observed.

Results

Experiment 1. Anti-Reserpine Activity of L-DOPA.

After the administration of L-DOPA to catatonic mice, all animals became active when given doses of 364 mg/kg or higher (Table 13). The level of activity was high compared to normal mice. Animals had a jerky gait and show toxic effects of L-DOPA such as rearing, salivating and jumping.

TABLE 13

Anti-reserpine activity of L-DOPA

| L-DOPA moiety | Response at 15 min. | |
|---|---|---|
| (mg/kg) | mouse 1 | mouse 2 |
| 9.1 | − | − |
| 91 | − | + |
| 364 | + | + |
| 637 | + | + |
| 910 | + | + |

− = remained catatonic; + = very active

Experiment 2. Anti-Reserpine activity of L-DOPA and L-DOPA-GTP$_2$.

L-DOPA caused catatonic mice to become very active (Table 14) as previously observed in Experiment 1. Animals which received miglyol only and low doses of L-DOPA-GTP$_2$ (9.1 and 91 mg DOPA/kg) did not recover. Mice which received higher doses of L-DOPA-GTP$_2$ (364 and 637 mg DOPA/kg) showed signs of recovery at 7 and 5 hr after administration, respectively. These animals moved slowly and sporadically and did not exhibit the high activity level and toxic effects that treatment with L-DOPA caused. These results indicate that L-DOPA-GTP$_2$ has the ability to form dopamine in catatonic mice brains. A slow release is suggested by the time taken for a response to occur and the nature of the response (slow movements at 5 to 8 hr versus over-active mouse at 20 minutes).

TABLE 14

Anti-Reserpine Activity of L-DOPA and L-DOPA-GTP$_2$

| DOPA moiety (mg/kg) | 20 min | 2 hr | 5 hr | 6 hr | 7 hr | 8 hr |
|---|---|---|---|---|---|---|
| 0 (3) | --- | --- | --- | --- | --- | --- |
| L-DOPA | | | | | | |
| 364 (1) | + | | | | | |
| 637 (1) | + | | | | | |
| DOPA-GTP$_2$ | | | | | | |
| 9.1 (2) | -- | -- | -- | -- | -- | -- |
| 91 (2) | -- | -- | -- | -- | -- | -- |
| 364 (2) | -- | -- | -- | -- | M − | MM |
| 637 (1) | − | − | M | M | M | M |

− = no response; + = very active; M = moving slowly (n) = number of animals in treatment.

Discussion

L-DOPA-GTP$_2$ has the ability to reverse reserpine-induced catatonia in mice. A slow release effect is shown after administration of L-DOPA-GTP$_2$ and toxic effects seen with L-DOPA were not evident.

EXAMPLE 15

Tumour Cytotoxicity Model: Test of Methotrexate and Chlorambucil and their fatty acid conjugates:

Protocol

Groups of C57 black mice were given an initiation dose of $2 \times 10^5$ B16 melanoma cells as an intradermal injection. The cells were suspended in MEM without serum. The abdomen was clipped and 100 µl of cells+MEM was injected. At 8–10 days after injection, spots of growing B16 tumours were seen at the injection site. The tumours were measured with a micrometer and photographed just prior to the injection of drug (day 8–10).

The cytotoxic drugs and their fatty acid conjugates were dissolved or suspended in 4:1 soy bean oil:ethyl oleate. A 10 mg/ml or a 20 mg/ml solution of each parent drug or the fatty acid conjugate made to the same molar concentration as the parent drug was then injected into the same region as the tumour at a dose of 0.5 mg or 1 mg. The tumours were then photographed, measured and re-injected every two to three days.

Tumour growth rates are shown in Table 15 and a statistical analysis of the effect of drug and drug conjugates is set out in Table 16.

TABLE 15

The effect of drug and drug conjugates on B16 Tumour Volume (mm$^3$) in C57 mice.

| Treatment | Day 1 | Day 3 | Day 5 | Day 6 | Day 7 | Drug Dose |
|---|---|---|---|---|---|---|
| Vehicle/1 | 6.3 | 26 | 54 | 99.3 | 174 | 0 |
| Vehicle/2 | 14.1 | 142 | 138.7 | 261.8 | 419 | 0 |
| Vehicle/3 | 19.8 | 14.1 | 254.1 | 410.3 | 780 | 0 |
| Vehicle/4 | 22.4 | 55.9 | 158.1 | 290.4 | 473 | 0 |
| MTX/1 | 0.5 | 13.6 | 73.5 | 125.1 | 190 | 0.5 mg |
| MTX/2 | 3.8 | 4.2 | 14.1 | 14.1 | 21 | 0.5 mg |
| MTX/3 | 14.1 | 30.4 | 86.0 | 215.0 | 234 | 0.5 mg |

TABLE 15-continued

The effect of drug and drug conjugates on B16 Tumour Volume ($mm^3$) in C57 mice.

| Treatment | Day 1 | Day 3 | Day 5 | Day 6 | Day 7 | Drug Dose |
|---|---|---|---|---|---|---|
| MTX/4 | 26 | 86 | 219.4 | 266.5 | 515 | 0.5 mg |
| $MTXGTP_2/1$ | 0.5 | 0 | 0 | 0 | 0 | 0.5 mg |
| $MTXGTP_2/2$ | 0.5 | 0 | 11.8 | 19.8 | 26 | 0.5 mg |
| $MTXGTP_2/3$ | 2.7 | 0 | 0 | 0 | 0 | 0.5 mg |
| $MTXGTP_2/4$ | 16.6 | 16.6 | 64.5 | 77.6 | 113 | 0.5 mg |
| $MTXGTP_2/5$ | 0.1 | 0.1 | 0.5 | 0.5 | 14 | 1.0 mg |
| $MTXGTP_2/6$ | 8.2 | 10.8 | 21.8 | 46.8 | 50 | 1.0 mg |
| $MTXGTP_2/7$ | 8.2 | 0 | 0 | 0 | 0 | 1.0 mg |
| $MTXGTP_2/8$ | 10.8 | 30.4 | 142.5 | 261.8 | 379 | 1.0 mg |
| Chlor/1 | 0.5 | 0.5 | 0 | 0 | 0 | 0.5 mg |
| Chlor/2 | 1.8 | 0 | 0 | 0 | 0 | 0.5 mg |
| Chlor/3 | 8.2 | 21.8 | 7.7 | 7.7 | 5.9 | 0.5 mg |
| Chlor/4 | 16.6 | 38.3 | 108.4 | 125.1 | 174.1 | 0.5 mg |
| $CGTP_2/1$ | 0.5 | 0.3 | 11.8 | 19.8 | 21.8 | 0.5 mg |
| $CGTP_2/2$ | 1.0 | 1 | 19.1 | 13.6 | 35.1 | 0.5 mg |
| $CGTP_2/3$ | 2.7 | 0 | 0.0 | 0 | 0 | 0.5 mg |
| $CGTP_2/4$ | 14.1 | 27.4 | 82.8 | 167.4 | 152.8 | 0.5 mg |
| $CGTP_2/5$ | 5 | 0 | 0 | 0 | 0 | 1.0 mg |
| $CGTP_2/6$ | 5 | 7.7 | 38.3 | 61.6 | 92.6 | 1.0 mg |
| $CGTP_2/7$ | 8.2 | 32.7 | 111.9 | 108.4 | 254.1 | 1.0 mg |
| $CGTP_2/8$ | 38.3 | 73.5 | 174.1 | 240.3 | 215.0 | 1.0 mg |

**MTX = Methotrexate
Chlor or (C) = Chlorambucil
**GTP2 = Gly-Tris-Dipalmitate
**/1 to /8 indicates individual mouse number i.e. $CGTP_2/4 = CGTP_2$ mouse number 4

TABLE 16

Means and standard errors of B16 tumour volumes on C57 mice. The value at each measurement date is adjusted for the variation in initial volume.

| TREATMENT | 13/11/95 | 15/11/95 | 16/11/95 | 17/11/95 |
|---|---|---|---|---|
| Vehicle | 3.58 (0.533) | 5.36 (0.8340) | 6.69 (1.00) | 6.33 (1.21) |
| Chlorambucil (0.5 mg) | 3.01 (0.610) | 3.29 (0.955) | 3.46 (1.15) | 3.65 (1.38) |
| $CGTP_2$ (0.5 mg) | 2.39 (0.523) | 4.07 (0.881) | 4.84 (1.06) | 4.90 (1.28) |
| $CGTP_2$ (1.0 mg) | 2.58 (0.523) | 3.89 (0.819) | 4.23 (0.98) | 4.84 (1.19) |
| $MTXGTP_2$ (0.5 mg) | 2.04 (0.565) | 3.37 (0.884) | 3.76 (1.06) | 4.03 (1.28) |
| $MTXGTP_2$ (1.0 mg) | 2.30 (0.536) | 3.40 (0.839) | 4.13 (1.01) | 4.89 (1.22) |
| Methotrexate (0.5 mg) | 3.58 (0.610) | 5.47 (0.955) | 6.07 (1.15) | 7.24 (1.38) |

Units are statistically modified tumour volume; figures in brackets are SD. All results are significant at the 95% level except that MTX is not significantly different from control. All others are sign. diff. from control but not from each other.

The results show:
1. There was no significant difference between the Vehicle and the Methotrexate (MTX) treated mice.
2. There was a significant difference between the vehicle/MTX and the $MTXGTP_2$ conjugates at the two different concentrations but there was no difference between the two conjugate groups.
3. There was a significant difference between the Vehicle and the chlorambucil, $CGTP_2$ (0.5mg) and $CGTP_2$ (1.0 mg) groups.
4. There was no difference between the chlorambucil group and the two conjugate groups or these with each other.
5. High toxicity was observed in chlorambucil test group (3 out of 7 mice died); no toxicity was observed with any other test group.
6. While there is no apparent advantage in cytotoxicity of chlorambucil conjugates compared to free chlorambucil the lower toxicity of the conjugates would offer a therapeutic advantage.

Conclusion

The present inventors have shown that nonsteroidal anti-inflammatory drugs when modified by the addition of one to three acyl derivatives of fatty acids exhibit prolonged activity compared to the unmodified parent when applied transdermally (see International Patent Application No. PCT/AU94/00440 the disclosure of which is incorporated herein by reference). The present inventors have now shown that other therapeutic agents when modified in a similar manner are biologically active and show altered activuty compared to the un modified drugs.

It will be appreciated by persons skilled in the art that numerous variations and/or modifications may be made to the invention as shown in the specific embodiments without departing from the spirit or scope of the invention as broadly described. The present embodiments are, therefore, to be considered in all respects as illustrative and not restrictive.

We claim:

1. A compound of the following formula:

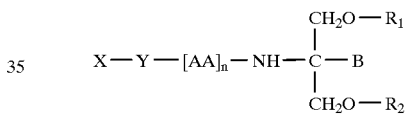

in which

X is methotrexate and is linked to Y via one of the carboxyl groups of methotrexate;

Y is absent or selected from the group consisting of:
(a) a compound having an amino acid group and a carboxyl group;
(b) a compound having an amino group and a sulfonic acid group;
(c) a compound having an hydroxyl group and a carboxyl group;
(d) a compound having an hydroxyl group and a sulfonic acid group;
(e) a compound having an hydroxyl group and a reactive halide group;
(f) a compound having a halide group and a carboxyl group;
(g) a compound having two reactive halide groups;
(h) a compound having an hydroxyl group and an aldehyde group; and
(i) an alkyleneoxide;

AA is an amino acid; n is a number from 0 to 5

B is H or $CH_2O-R_3$ $R_1$, $R_2$ and $R_3$ are the same or different and are either hydrogen, methyl, ethyl or an acyl group derived from a fatty acid, with the proviso that at least one of $R_1$, $R_2$ and $R_3$ is an acyl group derived from a fatty acid.

2. A compound as claimed in claim 1 in which Y is absent, an amino acid, glycolic acid, 3-hydroxypropionic acid or lactic acid, AA is not present or glycine or alanine, and the linkage is either an amide bond or an ester bond to the γ-carboxyl of the glutamyl moiety of methotrexate.

3. A compound according to claim 1, wherein Y is selected from the group consisting of a compound having an amino group and a sulfonic acid group.

4. A compound according to claim 1, wherein Y is selected from the group consisting of a a compound having an hydroxyl group and a carboxyl group.

5. A compound according to claim 1, wherein Y is selected from the group consisting of a compound having an hydroxyl group and a sulfonic acid group.

6. A compound according to claim 1, wherein Y is selected from the group consisting of a compound having an hydroxyl group and a reactive halide group.

7. A compound according to claim 1, wherein Y is selected from the group consisting of a compound having a halide group and a carboxyl group.

8. A compound according to claim 1, wherein Y is selected from the group consisting of a compound having two reactive halide groups.

9. A method of prolonging or altering the activity of methotrexate in a mammal in need of said activity comprising administering the compound in the form:

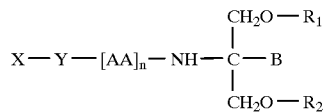

in which
X is methotrexate and is linked to Y via one of the carboxyl groups of methotrexate;
Y is absent or selected from the group consisting of:
(a) a compound having an amino acid group and a carboxyl group;
(b) a compound having an amino group and a sulfonic acid group;
(c) a compound having an hydroxyl group and a carboxyl group;
(d) a compound having an hydroxyl group and a sulfonic acid group;
(e) a compound having an hydroxyl group and a reactive halide group;
(f) a compound having a halide group and a carboxyl group;
(g) a compound having two reactive halide groups;
(h) a compound having an hydroxyl group and an aldehyde group; and
(i) an alkyleneoxide;

AA is an amino acid; n is a number from 0 to 5;

B is H or $CH_2O$—$R_3$;

$R_1$, $R_2$ and $R_3$ are the same or different and are either hydrogen, methyl, ethyl or an acyl group derived from a fatty acid, with the proviso that at least one of $R_1$, $R_2$ and $R_3$ is an acyl group derived from a fatty acid.

10. A method as claimed in claim 9 in which Y is absent, an amino acid, glycolic acid, 3-hydroxypropionic acid or lactic acid, AA is not present or glycine or alanine, and the linkage is either an amide bond or an ester bond to the γ-cart oxyl of the glutamyl moiety of methotrexate.

11. A method according to claim 9, wherein Y is selected from the group consisting of a compound having an amino group and a sulfonic acid group.

12. A method according to claim 9, wherein Y is selected from the group consisting of a a compound having an hydroxyl group and a carboxyl group.

13. A method according to claim 9, wherein Y is selected from the group consisting of a compound having an hydroxyl group and a sulfonic acid group.

14. A method according to claim 9, wherein Y is selected from the group consisting of a compound having an hydroxyl group and a reactive halide group.

15. A method according to claim 9, wherein Y is selected from the group consisting of a compound having a halide group and a carboxyl group.

16. A method according to claim 9, wherein Y is selected from the group consisting of a compound having two reactive halide groups.

* * * * *